(12) United States Patent
Alambeigi et al.

(10) Patent No.: US 12,703,117 B2
(45) Date of Patent: Aug. 11, 2026

(54) PROGRAMMABLE ELASTOMER ROBOT SYSTEM AND METHODS

(71) Applicant: Board of Regents, The University of Texas System, Austin, TX (US)

(72) Inventors: Farshid Alambeigi, Austin, TX (US); Uksang Yoo, Cortland, NY (US)

(73) Assignee: Board of Regents, The University of Texas System, Austin, TX (US)

( * ) Notice: Subject to any disclaimer, the term of this patent is extended or adjusted under 35 U.S.C. 154(b) by 113 days.

(21) Appl. No.: 18/559,610

(22) PCT Filed: May 10, 2022

(86) PCT No.: PCT/US2022/028448

§ 371 (c)(1),
(2) Date: Nov. 8, 2023

(87) PCT Pub. No.: WO2022/240794

PCT Pub. Date: Nov. 17, 2022

(65) Prior Publication Data

US 2024/0278440 A1 Aug. 22, 2024

Related U.S. Application Data

(60) Provisional application No. 63/186,317, filed on May 10, 2021.

(51) Int. Cl.
*B25J 9/14* (2006.01)
*B25J 18/02* (2006.01)

(Continued)

(52) U.S. Cl.
CPC ............ *B25J 19/007* (2013.01); *B25J 18/02* (2013.01); *B25J 18/06* (2013.01); *F15B 15/08* (2013.01);

(Continued)

(58) Field of Classification Search
CPC ..... B25J 9/14; B25J 18/02; B25J 18/06; B25J 19/007; F15B 15/08
See application file for complete search history.

(56) References Cited

U.S. PATENT DOCUMENTS 9,797,415 B2 * 10/2017 Martinez .................. B25J 9/142
9,945,397 B2 4/2018 Shepherd (Continued)

FOREIGN PATENT DOCUMENTS

CN 205329826 6/2016
KR 20030062303 7/2003
WO 9849976 11/1998

OTHER PUBLICATIONS

A. D. Marchese and D. Rus, "Design, kinematics, and control of a soft spatial fluidic elastomer manipulator," The International Journal of Robotics Research, vol. 35, pp. 840-869, Oct. 2015. Publisher: Sage Publications Ltd STM.

(Continued)

*Primary Examiner* — William C Joyce
(74) *Attorney, Agent, or Firm* — Riverside Law LLP

(57) ABSTRACT

An elastomer robot comprises a flexible internal structure comprising a first flexible material, wherein the internal structure is tunable, and a flexible external structure comprising a second flexible material, attached to the internal structure, including an aperture configured to accept a fluid, wherein the external structure is tunable. Methods of use and production are also disclosed.

17 Claims, 18 Drawing Sheets

(51) Int. Cl.

| | |
|---|---|
| ***B25J 18/06*** | (2006.01) |
| ***B25J 19/00*** | (2006.01) |
| ***F15B 15/08*** | (2006.01) |
| *A61M 25/01* | (2006.01) |
| *B29C 39/10* | (2006.01) |
| *B29K 83/00* | (2006.01) |
| *B29L 31/00* | (2006.01) |
| *B33Y 80/00* | (2015.01) |

(52) U.S. Cl.

CPC ............ *A61M 25/0155* (2013.01); *B25J 9/14* (2013.01); *B29C 39/10* (2013.01); *B29K 2083/00* (2013.01); *B29L 2031/748* (2013.01); *B33Y 80/00* (2014.12)

(56) References Cited

U.S. PATENT DOCUMENTS

| | | | |
|---|---|---|---|
| 10,788,058 | B2 | 9/2020 | Galloway |
| 2014/0109560 | A1 | 4/2014 | Ilievski |
| 2017/0087331 | A1 | 3/2017 | Cully |
| 2018/0303566 | A1 | 10/2018 | Soundararajan |
| 2019/0145435 | A1 | 5/2019 | Galloway |

OTHER PUBLICATIONS

B. Mosadegh, P. Polygerinos, C. Keplinger, S. Wennstedt, R. F. Shepherd, U. Gupta, J. Shim, K. Bertoldi, C. J. Walsh, and G. M. Whitesides, "Pneumatic Networks for Soft Robotics that Actuate Rapidly," Advanced Functional Materials, vol. 24, No. 15, pp. 2163-2170, 2014. https://onlinelibrary.wiley.com/doi/pdf/10.1002/adfm.201303288.

C. Lee, M. Kim, Y. J. Kim, N. Hong, S. Ryu, H. J. Kim, and S. Kim, "Soft robot review," International Journal of Control, Automation and Systems, vol. 15, pp. 3-15, Feb. 2017.

D. R. Ellis, M. P. Venter, and G. Venter, "Soft Pneumatic Actuator with Bimodal Bending Response Using a Single Pressure Source," Soft Robotics, Aug. 2020. Publisher: Mary Ann Liebert, Inc., publishers.

F. Connolly, C. J. Walsh, and K. Bertoldi, "Automatic design of fiber-reinforced soft actuators for trajectory matching," Proceedings of the National Academy of Sciences, vol. 114, No. 1, pp. 51-56, 2017. Publisher: National Academy of Sciences eprint: https://www.pnas.org/content/114/1/51.full.pdf.

F. Connolly, P. Polygerinos, C. J. Walsh, and K. Bertoldi, "Mechanical Programming of Soft Actuators by Varying Fiber Angle," Soft Robotics, vol. 2, pp. 26-32, Mar. 2015. Publisher: Mary Ann Liebert, Inc., publishers.

J. Fras, J. Glowka, and K. Althoefer, "Instant soft robot: A simple recipe for quick and easy manufacturing," in 2020 3rd IEEE International Conference on Soft Robotics (RoboSoft), pp. 482-488, Jul. 2020. Journal Abbreviation: 2020 3rd IEEE International Conference on Soft Robotics (RoboSoft).

J. Gwinner, "Non-linear elastic deformations," Acta Applicandae Mathematica, vol. 11, pp. 191-193, Feb. 1988.

K. Suzumori, T. Maeda, H. Wantabe, and T. Hisada, "Fiberless flexible microactuator designed by finite-element method," IEEE/ASME Transactions on Mechatronics, vol. 2, pp. 281-286, Dec. 1997.

L. Cao, X. Li, P. T. Phan, A. M. H. Tiong, J. Liu, and S. J. Phee, "A Novel Robotic Suturing System for Flexible Endoscopic Surgery," in 2019 International Conference on Robotics and Automation (ICRA), pp. 1514-1520, May 2019.

M. Kamata, S. Yamazaki, Y. Tanise, Y. Yamada, and T. Nakamura, "Morphological change in peristaltic crawling motion of a narrow pipe inspection robot inspired by earthworm's locomotion," Advanced Robotics, vol. 32, pp. 386-397, Apr. 2018. Publisher: Taylor & Francis.

P. Huy Nguyen, S. Sridar, W. Zhang, and P. Polygerinos, "Design and control of a 3-chambered fiber reinforced soft actuator with off-the shelf stretch sensors," International Journal of Intelligent Robotics and Applications, Apr. 2017.

P. Polygerinos, N. Correll, S. A. Morin, B. Mosadegh, C. D. Onal, K. Petersen, M. Cianchetti, M. T. Tolley, and R. F. Shepherd, "Soft Robotics: Review of Fluid-Driven Intrinsically Soft Devices; Manufacturing, Sensing, Control, and Applications in Human-Robot Interaction," Advanced Engineering Materials, vol. 19, Dec. 2017.

P. Polygerinos, S. Lyne, Z. Wang, L. F. Nicolini, B. Mosadegh, G. M. Whitesides, and C. J. Walsh, "Towards a soft pneumatic glove for hand rehabilitation," in 2013 IEEE/RSJ International Conference on Intelligent Robots and Systems, pp. 1512-1517, Nov. 2013. Journal Abbreviation: 2013 IEEE/RSJ International Conference on Intelligent Robots and Systems.

P. Polygerinos, Z. Wang, J. T. B. Overvelde, K. C. Galloway, R. J. Wood, K. Bertoldi, and C. J. Walsh, "Modeling of Soft Fiber Reinforced Bending Actuators," IEEE Transactions on Robotics, vol. 31, pp. 778-789, Jun. 2015.

P. Preechayasomboon and E. Rombokas, "Negshell casting: 3D-printed structured and sacrificial cores for soft robot fabrication," Plos One, vol. 15, p. e0234354, Jun. 2020. Publisher: Public Library of Science.

R. Deimel and O. Brock, "A novel type of compliant and underactuated robotic hand for dexterous grasping," The International Journal of Robotics Research, vol. 35, pp. 161-185, Aug. 2015. No. 1-3 Publisher: Sage Publications Ltd STM.

R. F. Shepherd, F. Ilievski, W. Choi, S. A. Morin, A. A. Stokes, A. D. Mazzeo, X. Chen, M. Wang, and G. M. Whitesides, "Multigait soft robot," Proceedings of the National Academy of Sciences, 2011. Publisher: National Academy of Sciences eprint: https://www.pnas.org/content/early/2011/11/21/1116564108.full.pdf.

S. Hashemi, D. Bentivegna, and W. Durfee, "Bone-Inspired Bending Soft Robot," Soft Robotics, Jul. 2020. Publisher: Mary Ann Liebert, Inc., publishers.

T. Nakajima, T. Yamaguchi, S. Wakabayashi, T. Arie, S. Akita, and K. Takei, "Transformable Pneumatic Balloon-Type Soft Robot Using Attachable Shells," Advanced Materials Technologies, vol. 5, p. 2000201, Jul. 2020. Publisher: John Wiley & Sons, Ltd.

Y. Elsayed, A. Vincensi, C. Lekakou, T. Geng, C. M. Saaj, T. Ranzani, M. Cianchetti, and A. Menciassi, "Finite Element Analysis and Design Optimization of a Pneumatically Actuating Silicone Module for Robotic Surgery Applications," Soft Robotics, vol. 1, pp. 255-262, Oct. 2014. Publisher: Mary Ann Liebert, Inc., publishers.

Y. Sun, Y. S. Song, and J. Paik, "Characterization of silicone rubber based soft pneumatic actuators," in 2013 IEEE/RSJ International Conference on Intelligent Robots and Systems, pp. 4446-4453, Nov. 2013. ISSN: 2153-0866.

Z. Wang, P. Polygerinos, J. T. B. Overvelde, K. C. Galloway, K. Bertoldi, and C. J. Walsh, "Interaction Forces of Soft Fiber Reinforced Bending Actuators," IEEE/ASME Transactions on Mechatronics, vol. 22, pp. 717-727, Apr. 2017.

* cited by examiner

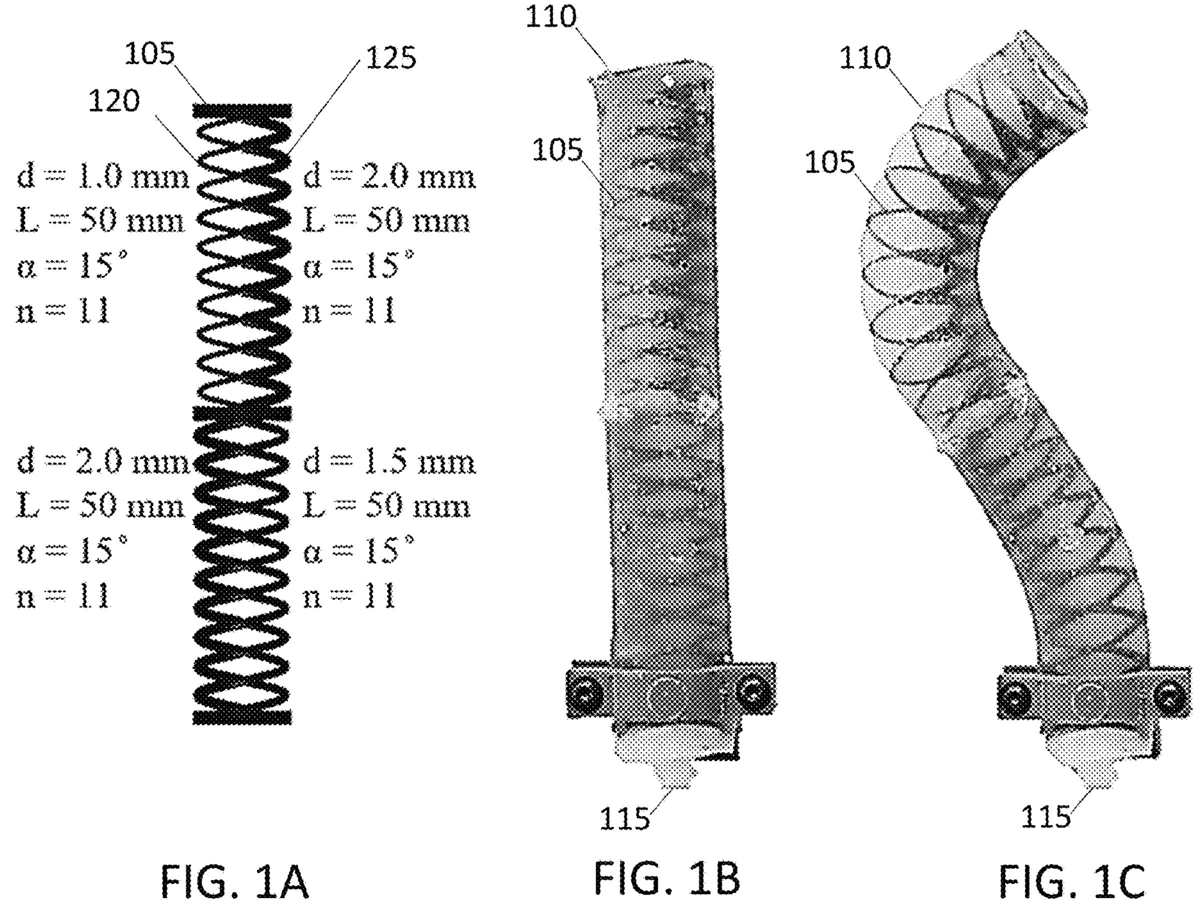
FIG. 1A
FIG. 1B
FIG. 1C

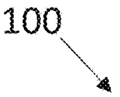
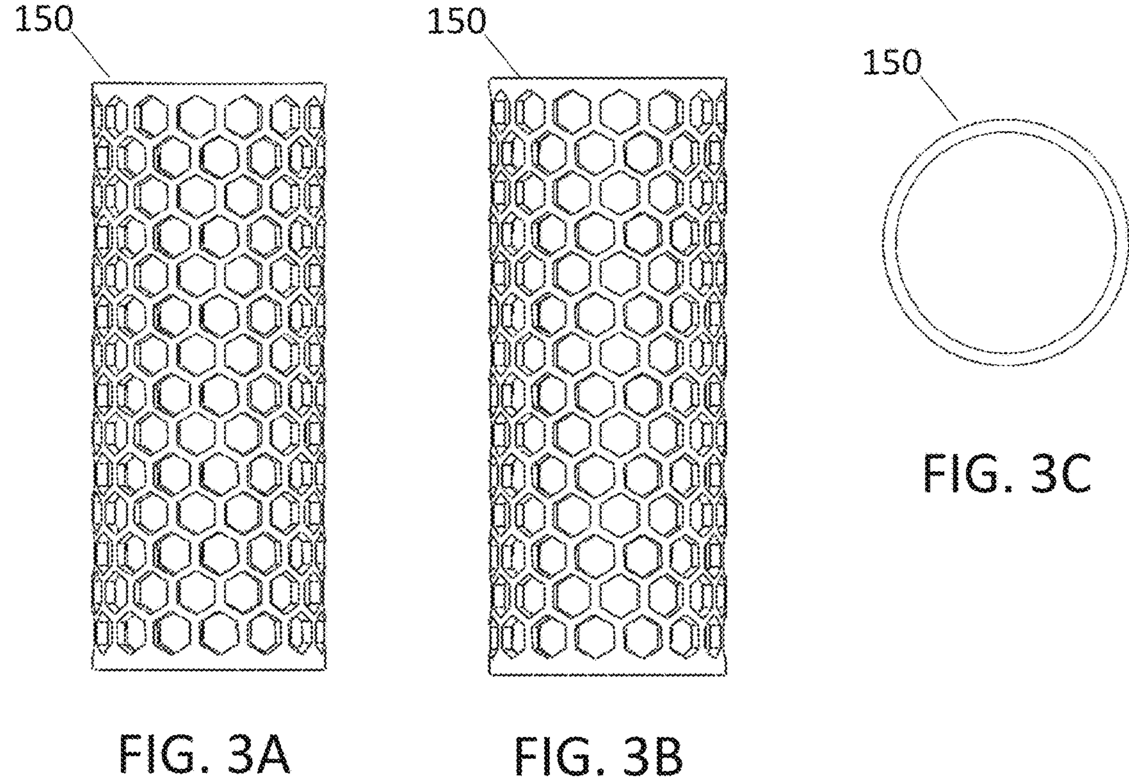
FIG. 3A
FIG. 3B
FIG. 3C

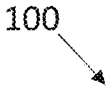
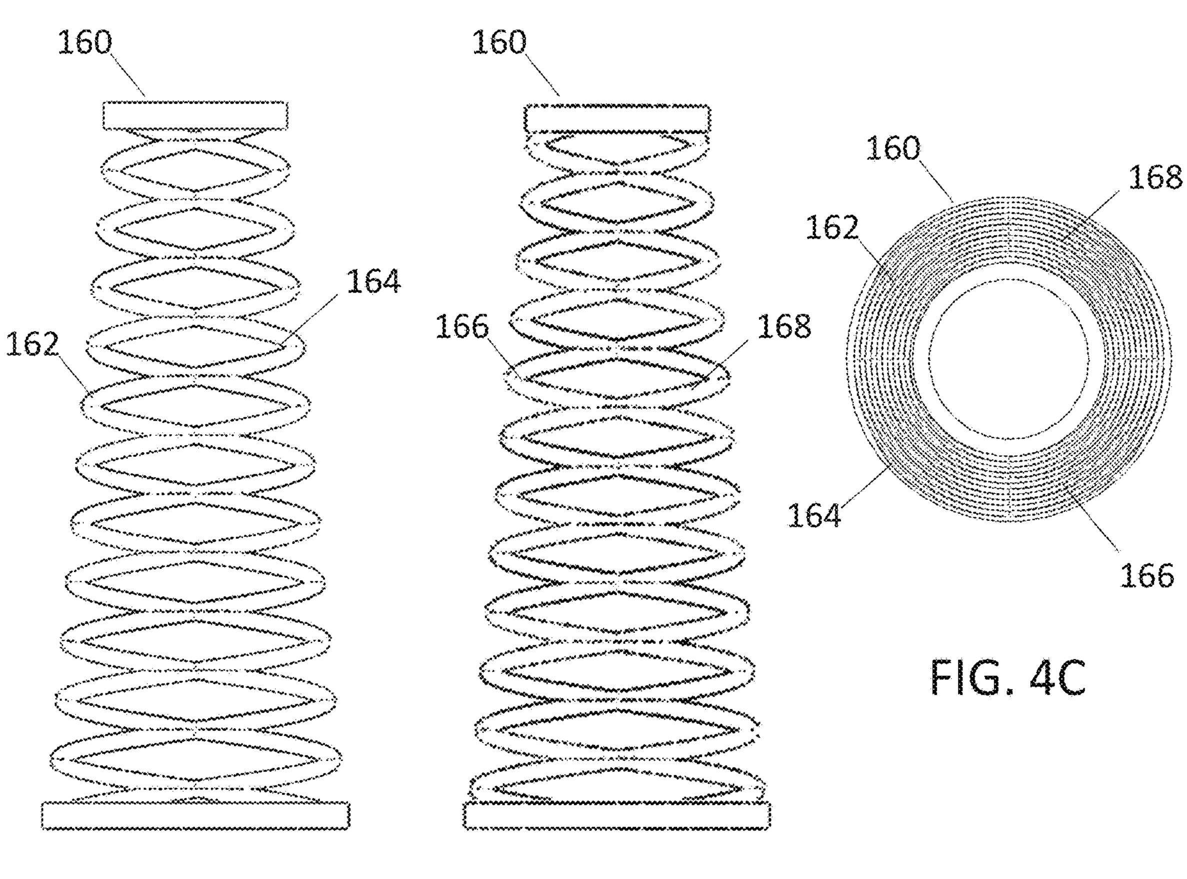
FIG. 4A FIG. 4B FIG. 4C

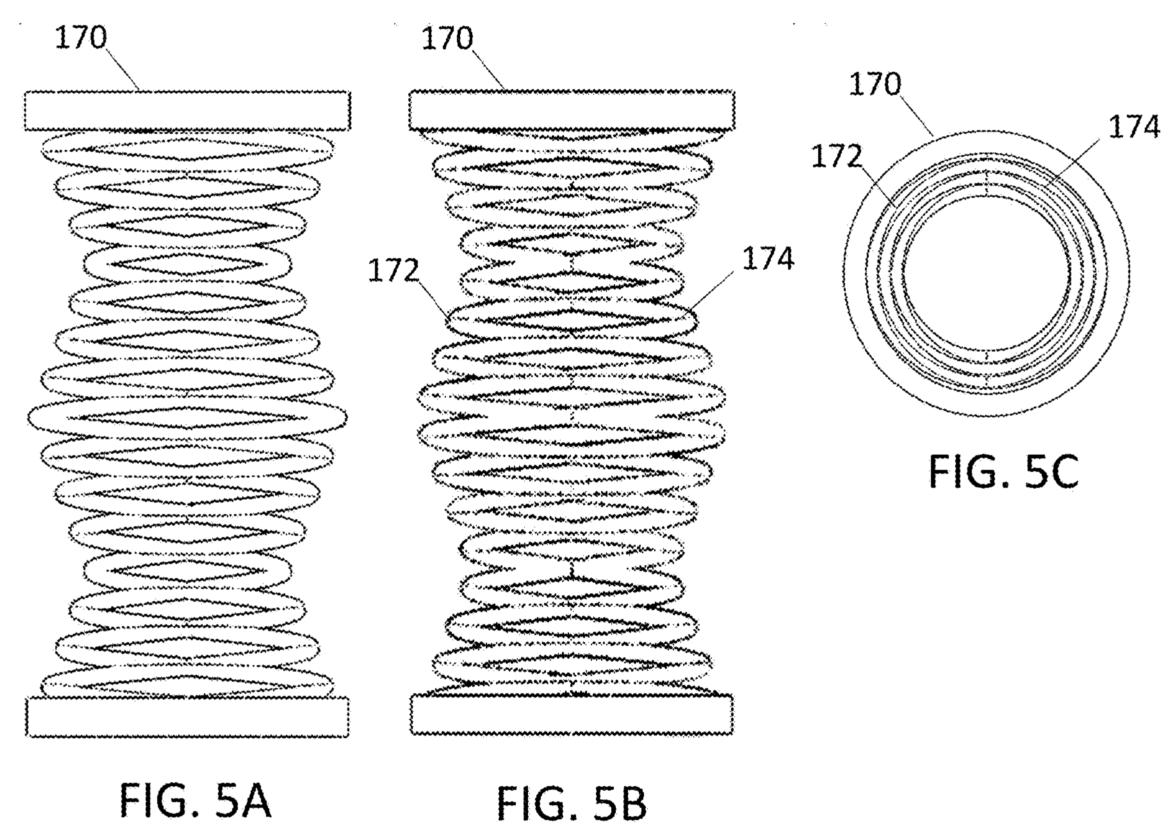
FIG. 5A
FIG. 5B
FIG. 5C

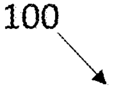
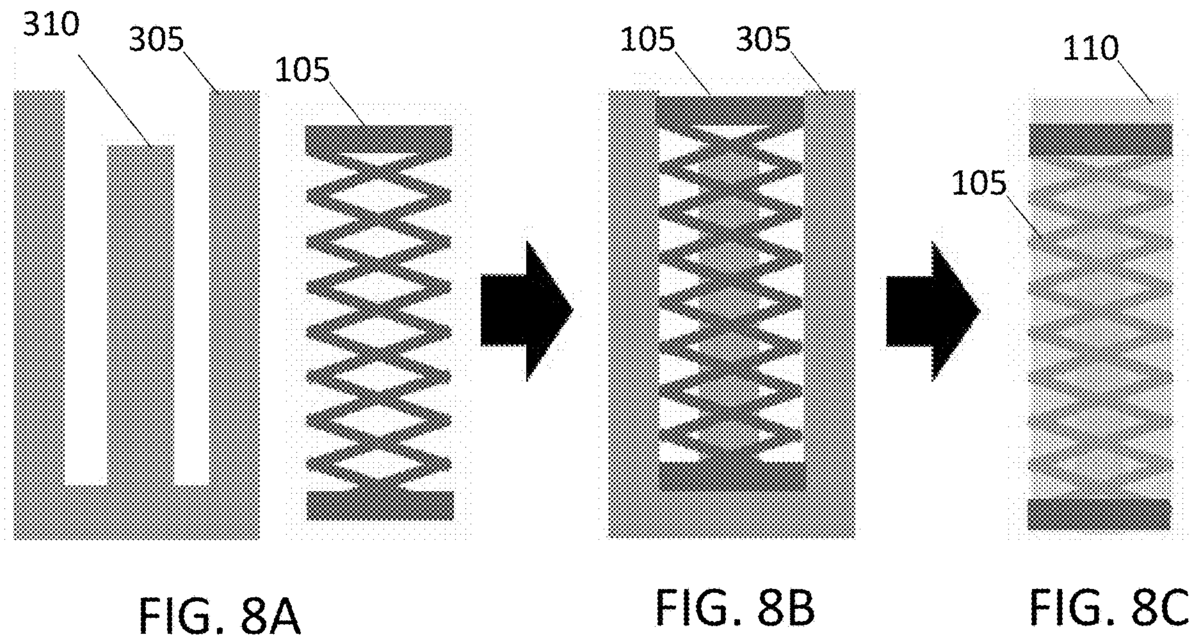
FIG. 8A
FIG. 8B
FIG. 8C

MATERIAL PROPERTIES OF THE HYBRID FEA

| Material | Purpose | Material Property* | | | |
|---|---|---|---|---|---|
| | | SH | TS | YM | ME |
| Ecoflex 00-35 | Primary Elastomer | 00-35 | 1.38 MPa | 69 kPa † | 900 % |
| FLGR02 | Constraining Structure | A-85 | 7.68 MPa | 10.05 MPa | 60 % |

* SH: Shore Hardness; TS: Tensile Strength; YM: Young's Modulus; ME: Max Elongation † 100% modulus

FIG. 11

COMPARISON OF THE EXPERIMENTAL RESULTS TO THE MODEL

| Material | $k_d$ | $D_m$ | $k_m$ | Error |
|---|---|---|---|---|
| FR | 5 N/m | 0.74 mm | 4.35 N/m | 13.00% |
| FR | 25 N/m | 1.11 mm | 22.2 N/m | 11.28% |
| FR | 125 N/m | 1.66 mm | 112.2 N/mm | 10.24% |

FR : Flexible Resin (SLA) $k_d$:Desired Stiffness $D_m$:Manufactured Coil Diameter $k_e$:Experimental stiffness $Error = (100)\frac{|k_c - k_e|}{k_c}$

FIG. 17

PROGRAMMABLE ELASTOMER ROBOT SYSTEM AND METHODS

CROSS-REFERENCE TO RELATED APPLICATIONS

This application is a U.S. national phase application filed under 35 U.S.C. § 371 claiming benefit to International Patent Application No. PCT/US2022/028448, filed May 10, 2022, which is entitled to priority of U.S. Provisional Patent Application No. 63/186,317, filed on May 10, 2021, the contents of which are each incorporated by reference herein in their entirety.

BACKGROUND

Soft elastomer robots are inherently advantaged in applications where the manipulator needs to curve and extend to reach the target in confined environments. Many applications necessitate robotic manipulators to be able to transverse nontrivial trajectories and interact with the confined environment safely. For example, in minimally invasive surgical procedures such as natural orifice transluminal endoscopic surgery (NOTES), the robotic manipulators need to be able to transverse through non-trivial curvilinear paths without damaging internal organs (see L. Cao et al., 2019 *International Conference on Robotics and Automation* (*ICRA*), pp. 1514-1520 May 2019). Similarly, robotic pipeline inspection requires the robotic manipulators to follow different types of passageways as narrow as 5 cm in diameter (see M. Kamata et al, *Advanced Robotics*, vol. 32, pp. 386-397, April 2018).

To address these challenges, researchers have suggested the use of elastomer robots, such as pneumatic elastomer actuators (PEAs) (see Y. Elsayed et al., *Soft Robotics*, vol. 1, pp. 255-262, October 2014) (see C. Lee et al., *International Journal of Control, Automation and Systems*, vol. 15, pp. 3-15, February 2017). Due to their constituent materials' compliance and the compressibility of air, PEAs have inherent advantages over conventional rigid robots for applications in which they need to safely morph and interact with the narrow and non-trivial passageways (see A. D. Marchese et al., *The International Journal of Robotics Research*, vol. 35, pp. 840-869, October 2015). The PEAs should display controlled actuation behaviors. Specifically, PEAs should be fully restricted in the radial direction to prevent thickening while axial stiffness can vary to allow desirable strain. It is also conceivable that in many applications, the PEA should bend and extend precisely to work in confined and constrained environments demanding the PEA to bend and extend predictably. As a corollary, the fabrication of these PEAs should be simple to reliably produce PEAs that behave predictably.

Previous PEA design approaches with strict radial constraints often have focused on pure bending or extension behaviors (see P. Polygerinos et al., *IEEE Transactions on Robotics*, vol. 31, pp. 778-789, June 2015) (see S. Hashemi et al., "Bone-Inspired Bending Soft Robot," *Soft Robotics*, July 2020). These approaches also relied on separate axial and radial strain-limiting layers, complicating both tuning and fabrication procedures (see R. Deimel et al., *The International Journal of Robotics Research*, vol. 35, pp. 161-185, August 2015).

For instance, elastomer thickness tuning is a simple approach to preprogramming bending and extension behavior of PEAs. A thicker elastomer wall displays higher stiffness and asymmetric thicknesses result in bending (see K. Suzumori et al., *IEEE/ASME Transactions on Mechatronics*, vol. 2, pp. 281-286, December 1997). A popular variation of this approach is to mold discrete pockets on the thin side which further reduces the stiffness and the bending radius (see P. Polygerinos et al., 2013 *IEEE/RSJ International Conference on Intelligent Robots and Systems*, pp. 1512-1517 November 2013) (see B. Mosadegh et al., *Advanced Functional Materials*, vol. 24, no. 15, pp. 2163-2170, 2014). Such approaches generally have simple fabrication steps because they involve only a homogeneous elastic material. However, these PEAs' exhibit unrestricted and significant radial expansion when actuated making them unsuitable for tasks in confined spaces (see K. Suzumori et al., *IEEE/ASME Transactions on Mechatronics*, vol. 2, pp. 281-286, December 1997) (see R. F. Shepherd et al., "Multigait soft robot," *Proceedings of the National Academy of Sciences,* 2011).

Additionally, fiber radial strain limiters are common modes of limiting radial strain (see P. Polygerinos et al., *IEEE Transactions on Robotics*, vol. 31, pp. 778-789, June 2015) (see F. Connolly et al., *Proceedings of the National Academy of Sciences*, vol. 114, no. 1, pp. 51-56, 2017). The fiber helices typically are wrapped manually to prevent the PEAs' overall diameters from increasing without restricting axial strain. Varying the fiber angles can alter the PEA's actuation behavior (see F. Connolly et al., *Proceedings of the National Academy of Sciences*, vol. 114, no. 1, pp. 51-56, 2017) (see F. Connolly et al., *Soft Robotics*, vol. 2, pp. 26-32, March 2015). However, manual wrapping of the fiber around a compliant elastomer core demand time-consuming manual steps that takes around 3 hours of labor with inherent human fabrication mistakes (see J. Fras et al., 2020 3*rd IEEE International Conference on Soft Robotics* (*RoboSoft*), pp. 482-488, July 2020). This process also results in fiber angle error in the range of ±5° (see F. Connolly et al., *Proceedings of the National Academy of Sciences*, vol. 114, no. 1, pp. 51-56, 2017). Such fabrication errors lead to discrepancy with the models and complicate the tuning of PEAs that solely rely on fibers. Varying the fiber angles and fiber turn density in PEAs leads to significant ballooning effects below 3.5 turns per centimeter, while PEA behavior is largely unaffected above 3.5 turns per centimeter fiber turn density (see Z. Wang et al., *IEEE/ASME Transactions on Mechatronics*, vol. 22, pp. 717-727, April 2017). This lower limit on the fiber turn density and limited impact of increasing the density above the limit demonstrates the limited tunability of the PEAs without ballooning. Furthermore, toward improving manufacturability of PEAs, prefabricated rings have been used to prevent radial strain, however, PEAs with embedded rings could only achieve bending with multiple parallel air chambers, making them too large and complicated for spatially constrained applications (see J. Fras et al., 2020 3*rd IEEE International Conference on Soft Robotics* (*RoboSoft*), pp. 482-488, July 2020).

Axial strain limiters such as a piece of fabric or bond paper are another approach that can be added to prevent surface strain of the stiff side (see P. Polygerinos et al., *IEEE Transactions on Robotics*, vol. 31, pp. 778-789, June 2015) (see R. Deimel et al. *The International Journal of Robotics Research*, vol. 35, pp. 161-185, August 2015) (see Y. Sun et al., 2013 *IEEE/RSJ International Conference on Intelligent Robots and Systems*, pp. 4446-4453 November 2013). Common axial strain limiting layers, such as bond papers, are entirely unextendible which translates to limited ability to adjust concurrent bending and extension behavior. Stiffer elastomers can also be added as an axial strain limiter to lead to concurrent bending and extension (see D. R. Ellis et al., "Soft Pneumatic Actuator with Bimodal Bending Response Using a Single Pressure Source," *Soft Robotics*, August 2020). However, embedding both a radial strain limiter and layers of stiffer elastomer necessarily adds to both the complexity and the overall dimensions of the robots, thus limiting their utility in confined spaces. 3D-printed rigid strain limiters have also been utilized, but they displayed severely constrained concurrent bending and extension behaviors because of the limiters' poor ability to handle large deformations in either direction (see T. Nakajima et al., *Advanced Materials Technologies*, vol. 5, p. 2000201, July 2020) (see P. Preechayasomboon et al., *PLOS ONE*, vol. 15, p. e0234354, June 2020).

Presently, elastomer robots, such as PEAs, suffer from difficult behavior tuning procedures, difficult fabrication, and a limited ability to tune actuation behavior, specifically pre-programed actuation behaviors based on tuned stiffnesses. Thus, there is a need in the art for improvements for fluidic elastomer robots.

SUMMARY

Some embodiments of the invention disclosed herein are set forth below, and any combination of these embodiments (or portions thereof) may be made to define another embodiment.

In one aspect, a programmable elastomer robot is comprised of a flexible internal structure comprising a first flexible material, wherein the internal structure is tunable, and a flexible external structure comprising a second flexible material, attached to the internal structure, including an aperture configured to accept a fluid, wherein the external structure is tunable.

In one embodiment, wherein the internal structure includes at least one section. In one embodiment, the at least one section includes at least one diameter. In one embodiment, the at least one diameter is a varying value. In one embodiment, the internal structure is cylindrical. In one embodiment, the internal structure is a quad-helical coil. In one embodiment, the quad-helical coil includes a first coil section with a first coil diameter, and a second coil section with a second coil diameter. In one embodiment, the internal structure is a hexagonal lattice. In one embodiment, the internal structure is conical. In one embodiment, the internal structure is a conical coil including a first coil section with a first coil diameter, a second coil section with a second coil diameter, a third coil section with a third coil diameter, and a fourth coil section with a fourth coil diameter. In one embodiment, the internal structure is sinusoidal. In one embodiment, the internal structure is a sinusoidal coil including a first coil section with a first coil diameter, and a second coil section with a second coil diameter. In one embodiment, wherein the internal structure is 3D printed. In one embodiment, the robot extends. In one embodiment, the robot bends. In one embodiment, the robot extends and bends concurrently. In one embodiment, the robot has a preprogrammed actuation behavior based on tunable parameters provided by a model. In one embodiment, the tunable parameters provided by the model are variable parameters. In one embodiment, the internal structure is self-supporting. In one embodiment, the internal structure comprises flexible resin. In one embodiment, the external structure comprises silicone rubber. In one embodiment, the external structure has a varying thickness. In one embodiment, the robot is further comprised of an internal cavity.

In another aspect, a programmable elastomer robot production method is comprised of creating a programmable design for an elastomer robot based on a model, the robot comprising a flexible tunable internal structure and a flexible tunable external structure, manufacturing the internal structure, manufacturing a mold, wherein the mold is a negative of a flexible tunable external structure, inserting the internal structure into the mold, pouring the external structure comprising a flexible compound material into the mold, waiting for the external structure to attach to the internal structure via curing, and removing the robot comprising the internal structure and the external structure from the mold.

In one embodiment, the internal structure is manufactured via 3D printing. In one embodiment, the internal structure is manufactured via forging. In one embodiment, the internal structure comprises a flexible resin. In one embodiment, the internal structure is cylindrical. In one embodiment, the internal structure is a quad-helical coil. In one embodiment, the quad-helical coil includes a first coil section with a first coil diameter, and a second coil section with a second coil diameter. In one embodiment, the internal structure is a hexagonal lattice. In one embodiment, the internal structure is conical. In one embodiment, the internal structure is a conical coil including a first coil section with a first coil diameter, a second coil section with a second coil diameter, a third coil section with a third coil diameter, and a fourth coil section with a fourth coil diameter. In one embodiment, the internal structure is sinusoidal. In one embodiment, the internal structure is a sinusoidal coil including a first coil section with a first coil diameter, and a second coil section with a second coil diameter. In one embodiment, the external structure comprises silicone rubber. In one embodiment, the internal structure is self-supporting. In one embodiment, the external structure has a varying thickness. In one embodiment, the robot has a preprogrammed actuation behavior based on tunable parameters provided by a model.

In another aspect, a method of using a programmable elastomer robot is comprised of providing a programmable elastomer robot as described herein, and supplying a fluid via the aperture, configured to apply a force to actuate the robot.

BRIEF DESCRIPTION OF THE DRAWINGS

The foregoing purposes and features, as well as other purposes and features, will become apparent with reference to the description and accompanying figures below, which are included to provide an understanding of the invention and constitute a part of the specification, in which like numerals represent like elements, and in which:

FIGS. 1A through 1C show an elastomer robot in accordance with some embodiments.

FIGS. 3A through 3C show an internal structure for an elastomer robot in accordance with some embodiments.

FIGS. 4A through 4C show an internal structure for an elastomer robot in accordance with some embodiments.

FIGS. 5A through 5C show an internal structure for an elastomer robot in accordance with some embodiments.

FIGS. 8A through 8C show an example molding processes for producing an elastomer robot in accordance with some embodiments.

FIG. 11 is a table showing details of example experimental materials utilized in the elastomer robot in accordance with some embodiments.

FIG. 17 is a table showing example experimental results compared to the model of an elastomer robot in accordance with some embodiments.

DETAILED DESCRIPTION

Figure 2:
FIG. 2 shows an internal structure for an elastomer robot in accordance with some embodiments.
Figure 2:
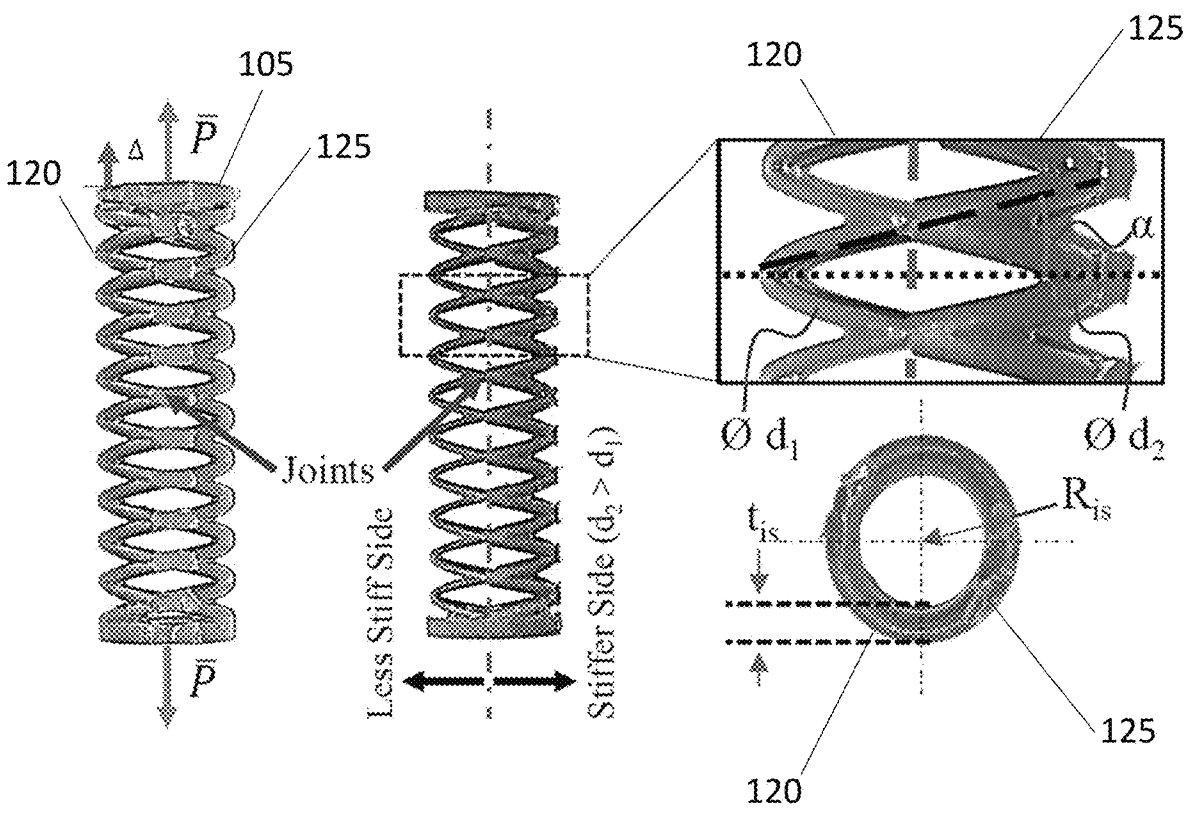

It is to be understood that the figures and descriptions of the present invention have been simplified to illustrate elements that are relevant for a clearer comprehension of the present invention, while eliminating, for the purpose of clarity, many other elements found in systems and methods of elastomer robots. Those of ordinary skill in the art may recognize that other elements and/or steps are desirable and/or required in implementing the present invention. However, because such elements and steps are well known in the art, and because they do not facilitate a better understanding of the present invention, a discussion of such elements and steps is not provided herein. The disclosure herein is directed to all such variations and modifications to such elements and methods known to those skilled in the art.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, and ±0.1% from the specified value, as such variations are appropriate.

Ranges: throughout this disclosure, various aspects of the invention can be presented in a range format. It should be understood that the description in range format is merely for convenience and brevity and should not be construed as an inflexible limitation on the scope of the invention. Where appropriate, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Referring now in detail to the drawings, in which like reference numerals indicate like parts or elements throughout the several views, in various embodiments, presented herein is an elastomer robot system and methods.

To address the above-mentioned limitations of the current approaches, disclosed is an elastomer robot system and methods. In one embodiment, the present invention comprises a directionally adjusted-stiffness pneumatic elastomer robot (DAS-PER) with a novel 3D printed quad-helical internal structure.

Some aspects of the present invention may be made using an additive manufacturing (AM) process. Among the most common forms of additive manufacturing are the various techniques that fall under the umbrella of "3D Printing", including but not limited to stereolithography (SLA), digital light processing (DLP), fused deposition modelling (FDM), selective laser sintering (SLS), selective laser melting (SLM), electronic beam melting (EBM), and laminated object manufacturing (LOM). These methods variously "build" a three-dimensional physical model of a part, one layer at a time, providing significant efficiencies in rapid prototyping and small-batch manufacturing. AM also makes possible the manufacture of parts with features that conventional subtractive manufacturing techniques (for example CNC milling) are unable to create.

Suitable materials for use in AM processes include, but are not limited to, using materials including but not limited to nylon, polyethylene terephthalate (PET), acrylonitrile butadiene styrene (ABS), resin, polylactic acid (PLA), polystyrene, and the like. In some embodiments, an AM process may comprise building a three-dimensional physical model from a single material, while in other embodiments, a single AM process may be configured to build the three-dimensional physical model from more than one material at the same time.

FIGS. 1A through 1C show an elastomer robot 100 in accordance with some embodiments. FIG. 1A shows an example of an asymmetric internal structure 105 with different directional biases to realize different bending behaviors. FIG. 1B shows an example of unactuated robot 100, where the robot comprises a flexible internal structure 105 comprising a first flexible material, and a flexible external structure 110 comprising a second flexible material, including an aperture 115, and attached to the internal structure 105. The internal structure 105 and the external structure 110 are tunable and can be preprogrammed to a defined actuation behavior including a programmed extension and/or bending behavior. In one embodiment, the aperture 115 is fluidly connected to an internal cavity. In one embodiment, the internal structure 105 is 3D printed. In one embodiment, the internal structure 105 is forged. In one embodiment, the internal structure 105 is a quad-helical coil. In one embodiment, the internal structure 105 is made from a polymer such as, for example, Flexible Resin (Formlabs™, FLFLGR02, PLA), thermoplastic polyurethanes (TPUs), metal, functionally graded materials (FGM), or any other suitable material or combination thereof. In some embodiments, the internal structure 105 is a heterogenous material, where the properties of the material vary throughout the internal structure 105. In one embodiment, the external structure 110 comprises silicone rubbers, such as Ecoflex™ 00-30, Ecoflex™

Dragon Skin, and Ecoflex™ 00-30, latex rubbers, polychloroprene, and any other natural or synthetic rubber, and combinations thereof. In some embodiments, the external structure 110 is a heterogenous material, where the properties of the material vary throughout the external structure 110.

In some embodiments, the material utilized for the internal structure 105 has a shore harness of A-50 to A-150, A-75 to A-100, A-80 to A-90, about A-85, or any other suitable shore hardness. In some embodiments, the material used for the internal structure 105 has a tensile strength of 1 to 15 MPa, 5 to 10 MPa, 7 to 8 MPa, about 7.68 MPa, or any other suitable tensile strength. In some embodiments, the material used for the internal structure 105 has a Young's modulus of 1 to 15 MPa, 7 to 13 MPa, 9 to 11 MPa, about 10.05 MPa, or any other suitable Young's modulus. In some embodiments, the material utilized for the internal structure 105 has a max elongation of 20% to 100%, 40% to 80%, 50% to 70%, about 60% or any other suitable max elongation percentage.

In some embodiments, the material utilized for the external structure 110 has a shore harness of 00-0 to 00-70, 00-20 to 00-50, 00-30 to 00-40, about 00-35, or any other suitable shore hardness. In some embodiments, the material used for the external structure 110 has a tensile strength of 0.5 to 2.5 MPa, 1 to 2 MPa, 1.25 to 1.75 MPa, about 1.38 MPa, or any other suitable tensile strength. In some embodiments, the material used for the external structure 110 has a Young's modulus of 20 to 100 kPa, 40 to 80 kPa, 65 to 75 kPa, about 69 kPa, or any other suitable Young's modulus. In some embodiments, the material utilized for the external structure 110 has a max elongation of 500% to 1500%, 800% to 1000%, about 900% or any other suitable max elongation percentage.

In some embodiments, the robot 100 has a stiffness of 1 to 50 N/m, 3 to 30 N/m, 1 to 10 N/m, 20 to 30 N/m, about 5 N/m, about 25 N/m, or any other suitable stiffness. In some embodiments, the robot 100 has a coil diameter of 0.1 to 2 mm, 0.5 to 1.5 mm, 0.5 to 1 mm, 1 to 1.5 mm, about 0.74 mm, about 1.11 mm, or any other suitable diameter.

In one embodiment, the external structure 110 comprises a flexible compound material. In one embodiment, the robot 100 is a directionally tuned pneumatic soft robot. FIG. 1C shows an example of actuated bending of an example robot 100 at 80 kPa. Note that the upper half of the example robot 100 displays a smaller bending radius than the bottom half from due to larger directional bias in the internal structure 105. In some embodiments, a plurality of internal structures 105 can be combined to produce robots 100 with a plurality of actuation behaviors. In one embodiment, the internal structure 105 is less elastic than the primary elastomer comprising the external structure 110. In one embodiment, the internal structure 105 is equal to or more elastic than the primary elastomer comprising the external structure 110.

FIG. 2 shows an internal structure 105 for an elastomer robot 100 in accordance with some embodiments. In particular, FIG. 2 shows an example design of a quad-helical internal structure 105. $\overline{P}$ represents the axial force applied on the internal structure 105 to elongate by Δ. The asymmetry in coil diameters $d_1$ and $d_2$ results in bending and extension behavior that is highly tunable. Note that in the illustrated example internal structure, $d_1<d_2$. Therefore, the side with coil diameter $d_1$ 120 is less stiff than the side with diameter $d_2$ 125.

Although the material constitution determines the bounds of the mechanical properties of the internal structure 105, the structural geometry of the robot 100 can be exploited to purposefully induce a particular deformation behavior. For example, many fiber-woven PEAs employ double helix configurations (see P. Huy Nguyen et al., *International Journal of Intelligent Robotics and Applications*, April 2017). Double helical structure constitutes the minimum number of spirals required to create a symmetric profile to force a linear expansion. These fiber restraints are often utilized to ideally restrict radial expansion of the PEA and allow axial elongation relatively unhindered. Studies of PEA actuation behavior tuning solely based on adjusting the fibers revealed that varying the fiber angles only significantly affect actuation behavior in the ranges where radial strain is not effectively restrained (see Z. Wang et al., *IEEE/ASME Transactions on Mechatronics*, vol. 22, pp. 717-727, April 2017).

For the flexible internal structure 105, however, it becomes possible to add axial stiffness without affecting its ability to restrain radial strain because of the structure's inherent rigidity and elastic resistance to deformation. Furthermore, asymmetry in axial stiffness can be preprogrammed to lead to bending. Such considerations also limit the number of spirals that the structure can realistically have as every added intertwined spiral will increase the axial stiffness. Additionally, the internal structure 105 should be able to support itself. However, the double helix configuration of a typical PEA does not satisfy this requirement because there is negligible resistance to bending in the plane perpendicular to the plane where the helices intersect. A compromise of the described design constraints is to supplement the double helix configuration with another double helix oriented with a 90 degree offset, thus creating a quad-helical coil structure. This remedy supplements the non-rigid plane of a double helix with stiffness of the rigid plane of another double helix. In one embodiment, the robot 100 internal structure 105 design has a fused quadruple helix configuration as shown in FIGS. 1A through 1C and FIG. 2.

In some embodiments, the number of coils n ranges from 1 to 1000, 3 to 500, 5 to 100, 5 to 50, 5 to 20, about 10, or any other suitable number. In some embodiments, the coil angle α ranges from 0° to 90°, 5° to 45°, 10° to 20°, about 15°, or any other suitable angle. In some embodiments the first diameter of the first coil section 120 and the second diameter of the second coil section 125 ranges from 0.01 mm to 10 m, 0.1 mm to 1 m, 0.5 mm to 10 cm, 1 mm to 5 mm, about 1 mm, about 1.5 mm, about 2 mm, or any other suitable diameter based on material properties, overall coil diameter, and geometry. These parameters can be adjusted and tuned based on the application of the robot 100 based on an actuation model. In some embodiments, the internal structure 105 includes at least one section, and the at least one section includes at least one diameter. In some embodiments, the at least one diameter of the at least one section is a varying value.

FIGS. 3A through 3C show another example embodiment of an internal structure 150 of the robot 100. FIGS. 3A, 3B and 3C show side, front and top views, respectively, of the internal structure 150. In the example shown, the internal structure 150 is cylindrically shaped and is comprised of a hexagonal lattice. Other geometric lattices can also be utilized such as, for example, lattices comprised of triangles, quadrangles, pentagons, heptagons, octagons, or any other suitable shape or combination thereof. In some embodiments, the lattice can have a tunable varying thickness and lattice size used to preprogram actuation behavior of the robot 100.

FIGS. 4A through 4C show another example embodiment of an internal structure 160 of the robot 100. FIGS. 4A, 4B and 4C show side, front and top views, respectively, of the internal structure 160. In the example shown, the internal structure 160 is conically shaped and is comprised of a multi-sectioned coil. In some embodiments, the internal structure 160 has a first coil section 162 with a first coil diameter, a second coil section 164 with a second coil diameter, a third coil section 166 with a third coil diameter, and a fourth coil section 168 with a fourth coil diameter. In some embodiments, the sections of the coil (162, 164, 166, 168) can have a tunable varying thicknesses and diameters used to preprogram actuation behavior of the robot 100. Any number of suitable coil sections can be utilized to provide the required actuation behavior.

FIGS. 5A through 5C show another example embodiment of an internal structure 170 of the robot 100. FIGS. 5A, 5B and 5C show side, front and top views, respectively, of the internal structure 170. In the example shown, the internal structure 170 is sinusoidally shaped and is comprised of a multi-sectioned coil. In some embodiments, the internal structure 170 has a first coil section 172 with a first coil diameter, and a second coil section 174 with a second coil diameter. In some embodiments, the sections of the coil (172, 174) can have a tunable varying thicknesses and diameters used to preprogram actuation behavior of the robot 100. Any number of suitable coil sections can be utilized to provide the required actuation behavior. In some embodiments, the stiffness of the coil can be related to the coil width, where, for example, a wider coil can result in a lower stiffness.

Figures 6A, 6B, 6C, 6D:
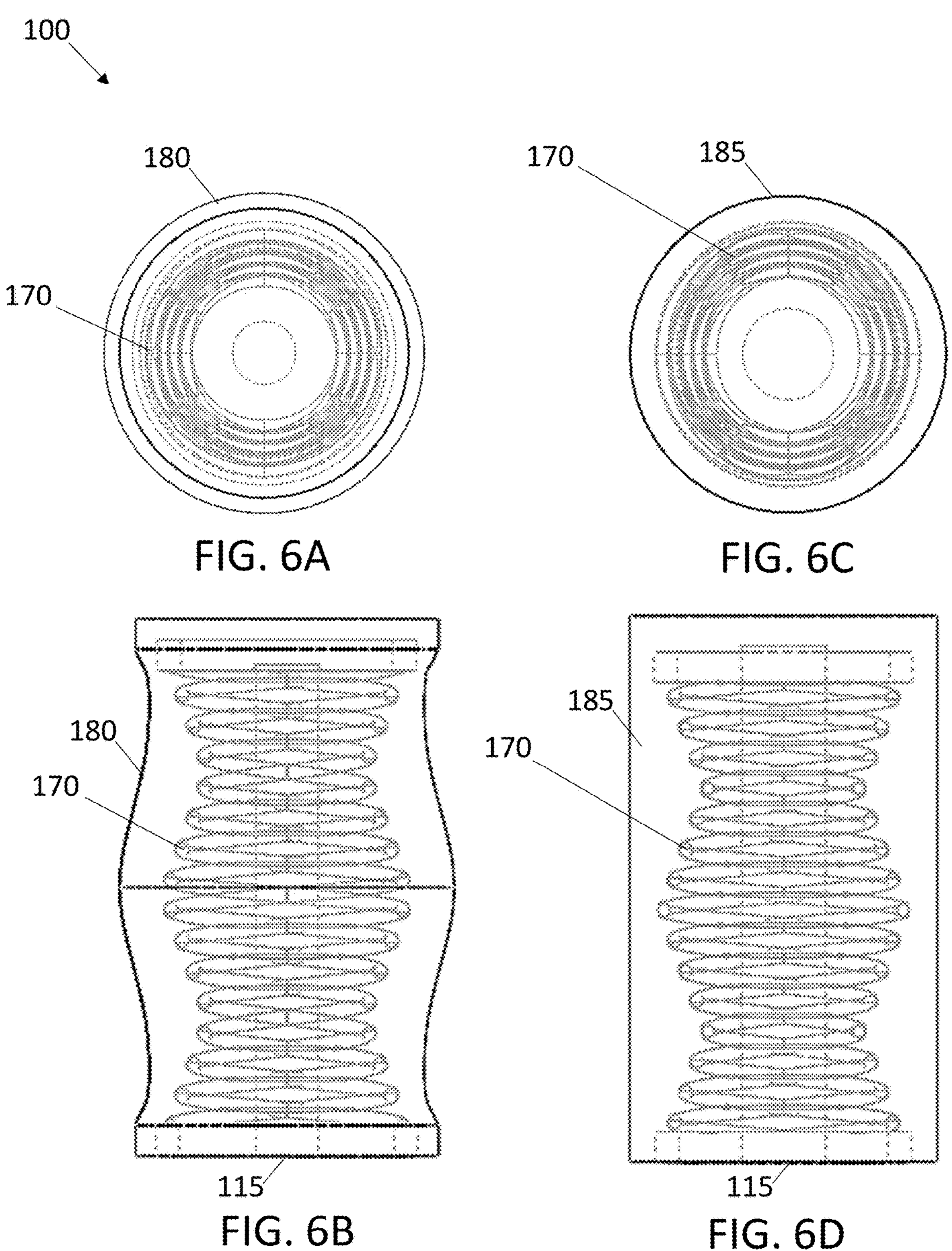
FIGS. 6A through 6D show elastomer robots in accordance with some embodiments.
Figure 7A:
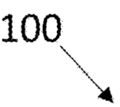
FIGS. 7A through 7B show an elastomer robot in accordance with some embodiments.
Figure 7A:
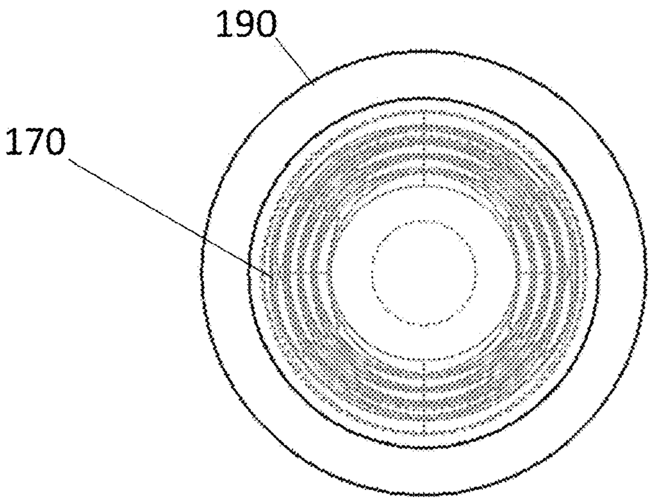
Figure 7B:
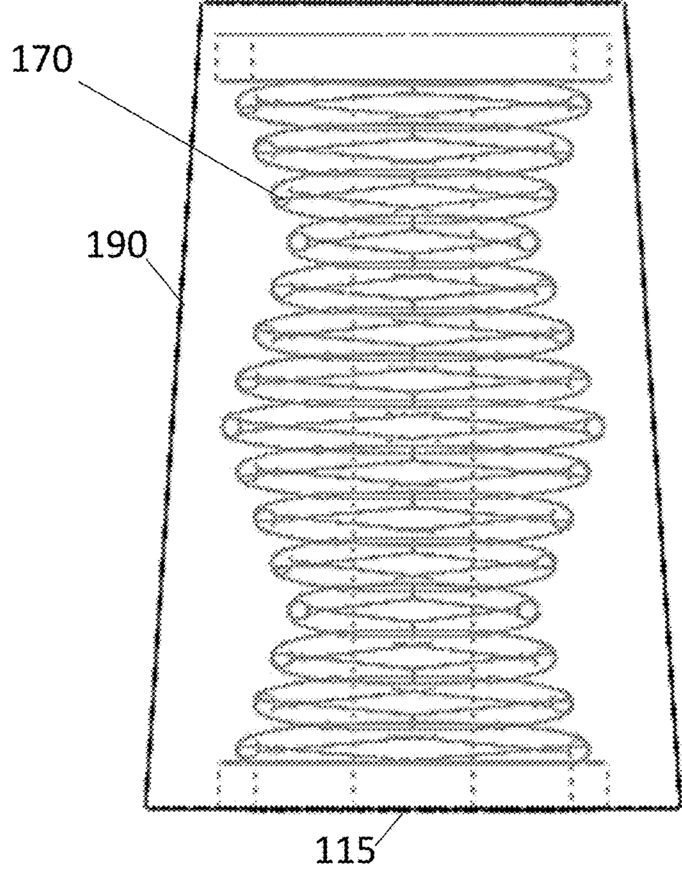

FIGS. 6A through 6D and FIGS. 7A and 7B show example embodiments of robots 100 with various examples of an external structure (180, 185, 190). FIGS. 6A and 6B depict top and side views, respectively, of an example robot comprised of a sinusoidal internal structure 170, and sinusoidal external structure 180 including an aperture 115. FIGS. 6C and 6D depict top and side views, respectively, of an example robot comprised of a sinusoidal internal structure 170, and cylindrical external structure 185 including an aperture 115. FIGS. 7A and 7B depict top and side views, respectively, of an example robot comprised of a sinusoidal internal structure 170, and conical external structure 190 including an aperture 115. Just as various parameters of the internal structure 170 can be tuned, the external structure (180, 185, 190) can also be tuned and shaped to provide preprogrammed to provide the required actuation behavior.

In order to preprogram and tune robots 100 for specific environments, a high-fidelity model that accounts for the robot's concurrent bending and extension is necessary. The model can provide the parameters necessary to create a design for, and ultimate produce, a robot of a specific size and with specific actuation behaviors for bending and extending via tuned stiffnesses of the internal and external structures. The model can provide the design parameters of the internal structure, including a general structure design and shape, a number of structure sections, and parameters of the sections including, but not limited to, structure diameters and how they vary, structure angles and how they vary, structure thicknesses and how they vary, and material compositions of the structure and how they vary. The model can also provide the design parameters of the external structure, including a general structure design and shape, and parameters of the structure design including, but not limited to, structure diameters and how they vary, structure thicknesses and how they vary, and material compositions of the structure and how they vary. In some embodiments, the parameters of the internal and external structures vary continuously throughout the structure. Furthermore, the design parameters of the robot 100 can be optimized based on the fluid used to actuate the robot 100.

The fabrication process of such robots also should not rely on manual ad-hoc fabrication steps that are error-prone and difficult to adjust. The fabrication steps can also benefit from eliminating the intermediate molding steps where the strain-limiting components are embedded. These improvements along with a high-fidelity model that can predict the robot's diverse array of bending and extension behaviors broaden potential applications of elastomer robots as they both simplify fabrication and allow the application to dictate precisely how the robot should behave.

FIGS. 8A through 8C show an example molding processes for producing an elastomer robot 100 in accordance with some embodiments. FIG. 8A depicts an internal structure 105 and a mold 305 with a cavity creating portion 310. FIG. 8B depicts the internal structure 105 placed inside the mold 305. FIG. 8C depicts a completed robot 100 which includes an external structure 110 attached to the internal structure 105. As shown in FIGS. 8A through 8C, the fabricated internal structure was inserted into a mold 305 that has a single tube in the center to create a cavity 310 that can accept a fluid in a single step.

In one example embodiment, Ecoflex™ 00-35 silicone components A and B were mixed as a 1:1 ratio by mass and poured into the mold 305. In certain embodiments, no postprocessing or additional molding steps outside of the primary mold 305 is required. By eliminating the intermediary manual step of prior robot production methods, the robot 100 fabrication process is significantly simplified as compared to the typical fabrication procedure of PEAs. In other embodiments the external structure 110 can comprise silicone rubbers, such as Ecoflex™ 00-30, Ecoflex™ Dragon Skin, and Ecoflex™ 00-30, latex rubbers, polychloroprene, and any other natural or synthetic rubber, and combinations thereof.

Figure 9:
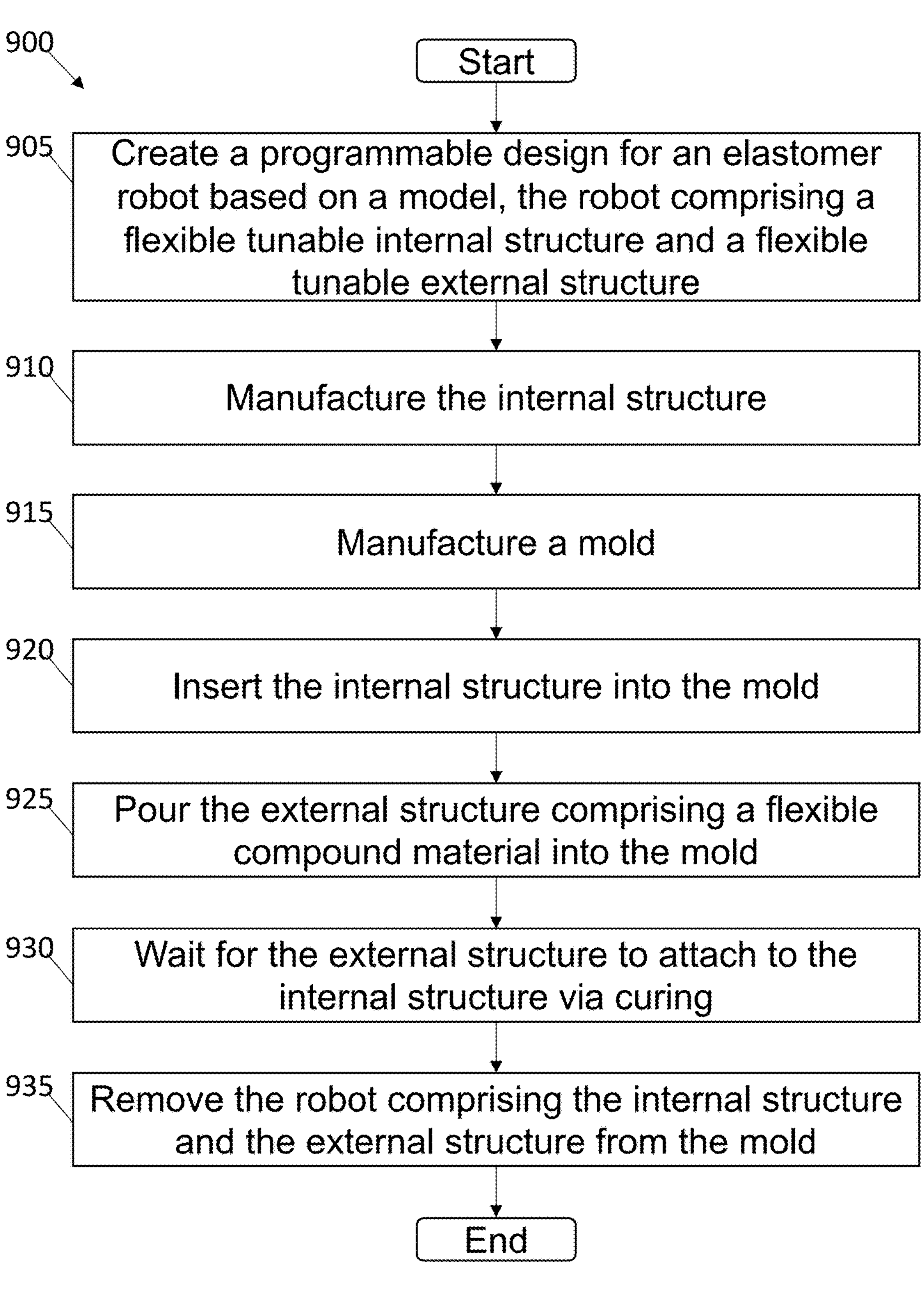
FIG. 9 is a flowchart showing an elastomer robot production method in accordance with some embodiments.

FIG. 9 is a flowchart showing a programmable elastomer robot 100 production method 900 in accordance with some embodiments. The method begins at Operation 905, where a programmable design for a flexible tunable internal structure (105, 150, 160, 170) and a flexible tunable external structure (110, 180, 185, 190) for an elastomer robot 100 based on a model is created. At Operation 910, the internal structure (105, 150, 160, 170) is manufactured. In some embodiments, the internal structure (105, 150, 160, 170) is manufactured via 3D printing. In some embodiments, the internal structure (105, 150, 160, 170) is manufactured via forging.

At Operation 915, a mold 305 is manufactured. The mold 305 can be a negative of the flexible tunable external structure (110, 180, 185, 190). At Operation 920, the internal structure (105, 150, 160, 170) is inserted into the mold 305. At Operation 925, an external structure (110, 180, 185, 190) comprising a flexible compound material is poured into the mold. At Operation 930, the external structure (110, 180, 185, 190) is attached to the internal structure (105, 150, 160, 170) via curing by waiting a set amount of time. The method 900 ends at Operation 935, where the robot 100 comprising the internal structure (105, 150, 160, 170) and the external structure (110, 180, 185, 190) is removed from the mold 305.

In one embodiment, the internal structure (105, 150, 160, 170) comprises a flexible resin. In one embodiment, the internal structure (105, 150, 160, 170) is cylindrical. In one embodiment, the internal structure 105 is a quad-helical coil. In one embodiment, the quad-helical coil includes a first coil section 120 with a first coil diameter, and a second coil section 125 with a second coil diameter. In one embodiment, the internal structure 150 is a hexagonal lattice. In one embodiment, the internal structure (105, 150, 160, 170) is conical. In one embodiment, the internal structure 160 is a conical coil including a first coil section 162 with a first coil diameter, a second coil section 164 with a second coil diameter, a third coil section 166 with a third coil diameter, and a fourth coil section 168 with a fourth coil diameter. In one embodiment, the internal structure (105, 150, 160, 170) is sinusoidal. In one embodiment, the internal structure 170 is a sinusoidal coil including a first coil section 172 with a first coil diameter, and a second coil section 174 with a second coil diameter.

In one embodiment, the external structure (110, 180, 185, 190) comprises silicone rubber. In one embodiment, the external structure (110, 180, 185, 190) has a varying thickness. In one embodiment, the internal structure (105, 150, 160, 170) is self-supporting. In one embodiment, the internal structure (105, 150, 160, 170) and the external structure (110, 180, 185, 190) are tunable via design parameters to provide specific bending, extension and actuation attributes. In one embodiment, the robot 100 has a preprogrammed actuation behavior based on tunable parameters provided by a model. In one embodiment, the tunable parameters provided by the model are variable parameters.

Figure 10:
FIG. 10 is a flowchart showing a method of using an elastomer robot in accordance with some embodiments.
Figure 10:
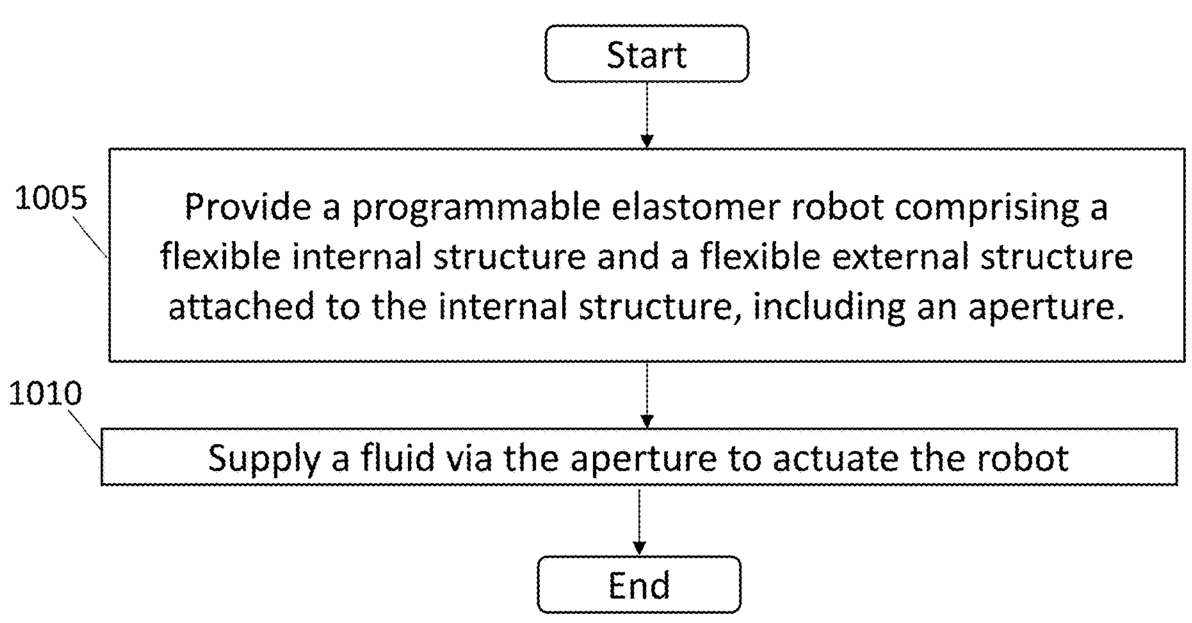

FIG. 10 is a flow chart showing a method 1000 of using a programmable elastomer robot 100 in accordance with some embodiments. Example uses for the robot 100 include surgical applications, pipeline inspection, medical imaging, medical diagnostic applications such as endoscopy and biopsy, for example, fruit picking and manipulation, grasping of delicate and deformable objects, and manufacturing, assembly and packing of goods, among other suitable uses and combinations known in the art.

The method 1000 begins at Operation 1005, where a programmable elastomer robot 100 is provided. In one embodiment, the robot 100 comprises a flexible internal structure (105, 150, 160, 170) comprising a first flexible material, wherein the internal structure is tunable, and a flexible external structure (110, 180, 185, 190) comprising a second flexible material, attached to the internal structure, including an aperture 115 configured to accept a fluid, wherein the external structure is tunable.

In one embodiment, the internal structure (105, 150, 160, 170) is 3D printed. In one embodiment, the internal structure (105, 150, 160, 170) is forged. In one embodiment, the internal structure 105 is a quad-helical coil. In one embodiment, the quad-helical coil includes a first coil section 120 with a first coil diameter, and a second coil section 125 with a second coil diameter. In one embodiment, the aperture 115 is fluidly connected to an internal cavity.

The method 1000 ends at Operation 1010, where a fluid is supplied via the aperture 115 to manipulate the robot 100. The fluid applies a fluid force to the robot 100 which forces the actuation of the robot 100 based on the strain and stiffness properties of the internal structure (105, 150, 160, 170) and the external structure (110, 180, 185, 190). In one embodiment, the fluid passes through the aperture 115 and into the internal cavity. In one embodiment the fluid is air. In one embodiment the fluid is water. In one embodiment, the fluid is a hydraulic fluid. In one embodiment, the fluid is at least one of air, water, hydraulic fluid, and any suitable fluid or combination thereof.

EXPERIMENTAL EXAMPLES

The invention is now described with reference to the following Examples. These Examples are provided for the purpose of illustration only and the invention should in no way be construed as being limited to these Examples, but rather should be construed to encompass any and all variations which become evident as a result of the teaching provided herein.

Without further description, it is believed that one of ordinary skill in the art can, using the preceding description and the following illustrative examples, make and utilize the present invention and practice the claimed methods. The following working examples therefore, specifically point out the preferred embodiments of the present invention, and are not to be construed as limiting in any way the remainder of the disclosure.

In one embodiment, the robot can be purposefully tuned via two design parameters (i.e., the asymmetric diameters of the internal structure helices) to achieve a diverse set of bending and extension configurations without experiencing a radial expansion. To deterministically tune the internal structure's stiffness and, subsequently, the bending and extension behavior of the robot, strain energy-based analytical models were developed for both and internal structure and external structure. Using these analytical models, two variations of the disclosed robot were designed and fabricated using a hybrid additive manufacturing and molding procedure. The disclosed modeling, design, and fabrication procedures were then evaluated with physical experiments that assessed internal structure stiffness and DAS-PER actuation behavior.

Some example design requirements were considered to meet the abovementioned needs. First, it is advantageous if the robot displays significantly diverse concurrent bending and extension behaviors. Second, it is advantageous if the robot is easily tunable with a limited set of parameters. Third, it is advantageous if the robot 100 can be produced with simple fabrication procedures with a minimum number of molding steps. The internal structure material constitution and design are fundamental in determining the efficacy of the robot.

FIG. 11 is a table showing details of example experimental materials utilized in the elastomer robot 100 in accordance with some embodiments. Ecoflex 00-35 silicone (Smooth-On, Ecoflex™ 00-35) was selected as the elastomer for the external structure 110. The material was readily available and displayed large strain before breaking. The table of FIG. 11 summarizes the material properties of Ecoflex 00-35 silicone. The Ecoflex 00-35 has a shore harness of 00-35, a tensile strength of 1.38 MPa, a Young's modulus of 69 kPa, and a max elongation of 900%.

The material used for the internal structure 105 of the robot 100 is both flexible and inextensible (see P. Polygerinos et al., *Advanced Engineering Materials*, vol. 19, December 2017). The flexibility of the material is crucial in allowing the internal structure 105 to expand in the desirable axial direction. Meanwhile, stretching in the internal structure 105 (i.e. elastic lengthening of the material) would be detrimental to the proper efficacy of the structure leading to radial expansion of the robot 100. Two additional material criteria for the internal structure 105 were also considered. First the material should be available for additive fabrication. Second, the material should maintain a minimum level of rigidity, where the fabricated structure should be able to sustain an upright freestanding position. The main reason for the latter requirement is to simplify the molding process to a single step. If the internal structure 105 is not able to stay upright on its own, there needs to be additional support structures to supplement the molds and the internal structure (see J. Fras et al., 2020 *3rd IEEE International Conference on Soft Robotics* (*RoboSoft*), pp. 482-488, July 2020).

Considering the above criteria, Flexible Resin (Formlabs™, FLFLGR02) was selected to be specifically compatible with the Formlabs™ Form 3 fabricator. Flexible Resin had the advantage of being readily available and having the desired material properties needed. The disclosed design is largely elastomer agnostic, given that it is sufficiently flexible and elastic enough to be inflated. The material property of the Flexible Resin is listed in the table of FIG. 11 and was tested with a universal test system (MTS Criterion® Series 40). The Formlabs™ FLGR02 has a shore harness of A-85, a tensile strength of 7.68 MPa, a Young's modulus of 10.05 MPa, and a max elongation of 60%.

Quad-Helical Internal Structure Modeling

Figure 12:
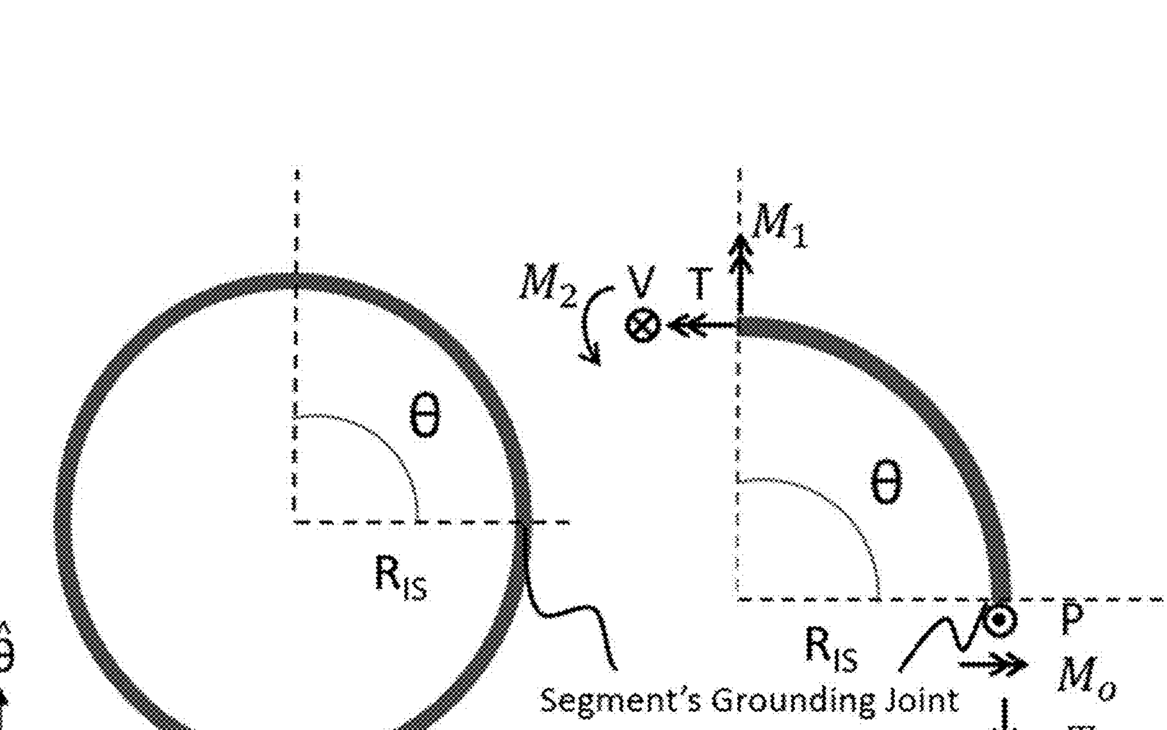
FIG. 12 shows a top view of the internal structure of an elastomer robot for example experimental analysis and modeling in accordance with some embodiments.

FIG. 12 shows a top view of the internal structure of an elastomer robot for example experimental analysis and modeling in accordance with some embodiments. Castigliano's Method was used for analysis. The segment extends 90 degrees from the top view as it connects from one joint to the next. P, $M_0$, $T_0$ and, $C_0$ are the reaction forces from the grounding joint.

A significant benefit of the robot 100 is its tunability. Fabricators can easily change parameters of the internal structure 105 to approach desired actuation behavior for the particular application. However, to maximize the benefits of tunability, a high-fidelity model was needed to avoid the inefficient trial-and-error based tuning procedures with numerous physical experimental trials. The model enables intentional model-based design. Some modeling assumptions made included that the radial and circumferential stresses are vanishing, the robot has constant curvature (a bending radius and angle define the shape), the internal structure 105 has constant (Hookean) stiffness, the silicone acts as a neo-Hookean solid, and that the silicone displacement can be modeled as displacement of a hollow cylinder with the thickness of the internal structure 105.

The first assumption is nearly always taken by researchers when modeling bending of radially constrained PEAs (see P. Polygerinos et al., *IEEE Transactions on Robotics*, vol. 31, pp. 778-789, June 2015). To validate the constant curvature assumption, three points were taken from the robot 100 to be compared with the model during experiments. The alignment of the points placed in the middle and at the distal tip to the model output can verify that robots 100 follow a constant curvature actuation behavior. Force-displacement experiments were conducted with the internal structure 105 to validate that it displays a constant stiffness within the relevant strain range. The assumptions with the silicone behavior properties were validated concurrently with the result of the actuation experiments.

To analytically design and tune the stiffness of the internal structure 105 presented in FIGS. 1A through 1C and FIG. 2, a model based on Castigliano's method was formulated (see F. Beer et al., *Mechanics of Materials*. McGraw-Hill Education, 2011). The total axial deformation of the elastic internal structure 105 was calculated based on the partial derivatives of its strain energy. Of note, this calculation depends on the internal structure design parameters (i.e., length, diameter, and double helix geometry of the internal structure), as well as the exerted axial force. This model is then used to evaluate the axial stiffness of the internal structure 105.

As shown in FIGS. 1A through 1C and FIG. 2, the internal structure 105 is constructed by repeating a segment depicted in FIG. 12. The mechanics of the flexible internal structure 105 was evaluated by analyzing the repeated segment between two connecting points, where one end of the segment is anchored to the other segments. The overall energy of the structure is the linear combination of the associated energy with each of these segments. Following the Castigliano's Method, the strain energy of the internal structure can be calculated as the following:

$$U = \int_0^{\alpha} \left[ \frac{1}{2}\frac{T_0^2}{GJ} + \frac{1}{2}\frac{M_1^2}{EI_1} + \frac{1}{2}\frac{M_2^2}{EI_2} \right] \frac{R}{\cos\alpha} d\theta \tag{1}$$

where $M_1$, $M_2$, and T are the internal moments and torque of the structure, respectively. Angles α and θ are defined based on FIG. 12. E is Young's modulus, I is the second moment of area of the cross-section, and R is the radius of the internal structure. G is shear modulus and J is the second moment of area around its origin. Since the cross-section of the coils are circular and symmetric, future notations will use/to denote both $I_1$ and $I_2$. Also, based on the Castigliano's method, the displacements of the grounding joints are zero, thus:

$$\frac{dU}{dT_0} = 0, \frac{dU}{dC_0} = 0, \frac{dU}{dM_0} = 0 \tag{2}$$

Considering Equations (1) and (2), the internal structure deflection Δ (i.e., elongation), can be computed by derivation of the strain energy with respect to the applied axial force P (shown in FIG. 12). It is worth noting that the internal moments and torque expressed in Equation (1) are a function of the axial applied force.

$$\frac{dU}{dP} = \Delta \tag{3}$$

Based on FIG. 12, the total moment around the z-axis is set to 0 (equilibrium conditions) and the resulting relation is the following:

$$\sum M_z = 0 = -C_0 + T\sin\alpha + M_2\cos\alpha \tag{4}$$

Similarly, the moment summation around 0 and r in the cylindrical coordinates were computed as the following:

$$\sum M_\theta = 0 = -M_0\sin\theta - T_0\cos\theta + T \tag{5}$$

$$\sum M_r = 0 = M_0\cos\theta - T_0\sin\theta + M_1 - PR\sin\theta$$

From Equation (3), $M_1$ was solved for as the following:

$$M_1 = T_0\sin\theta - M_0\cos\theta + PR\sin\theta \tag{7}$$

From Equations (1) and (2), T and $M_2$ were solved for as the following:

$$T = C_0\sin\alpha + M_0\cos\alpha\sin\theta + T_0\cos\alpha\cos\theta - PR(1-\cos\theta)\sin\alpha \quad (8)$$

$$M_2 = C_0\cos\alpha - M_0\sin\alpha\sin\theta - T_0\sin\alpha\cos\theta + PR(1-\cos\theta)\sin\alpha$$

Equilibrium conditions in the cylindrical coordinate system defined by Equations (4), (5), and (6) yield the components of the geometry-based relationships of Equations (7), (8), (9). Additionally, with the boundary conditions Equation (2), Equation (1) can be fully defined. Furthermore, as a result of Equation (3), deformation of a single segment in a robot 100 internal structure 105 can be characterized.

To calculate the overall strain energy of the internal structure 105, the analysis of a single segment must be scaled up to the full internal structure 105. The internal structure 105 has morphological symmetry in the front and side planes (see FIG. 2). When the internal structure 105 is cut through any plane parallel to the top plane, it can be observed that there are always four segments exposed. This observation along with the internal structure's symmetry means that each segment carries an equal share of the load applied in equilibrium. Hence, let $\overline{P}$ denote the force applied to the overall core axial stiffness structure, the relationship between P and $\overline{P}$ can be obtained as the following:

$$P = \frac{\overline{P}}{q} \quad (10)$$

where q denotes the number of segments of interest in the same joint-layer. For example, q can be set to 4 when working with symmetric internal structures to find the overall stiffness. In cases where the internal structure 105 is asymmetric, q can be set as 2 to find the half side's stiffness. The segments' deformation also adds to each other for every joint-layer. Then, if $\overline{\Delta}$ is the deflection of the overall core structure and n is the number of joints down one side of the structure, the relationship between $\Delta$ and $\overline{\Delta}$ can be computed as:

$$\overline{\Delta} = 2(n-1)\Delta \quad (11)$$

Considering (10) and (11), the axial stiffness, $\overline{k}$ of the core structure can be determined as:

$$\overline{k} = \frac{q}{2(n-1)}\frac{P}{\Delta} \quad (12)$$

Neo-Hookean Silicone Model

Incompressible Neo-Hookean theory defines strain energy W as the following:

$$W = C_1(I_1 - 3) \quad (13)$$

where $C_1$ is a material constant defined as part of the overarching Ogden material theory and $I_1$ is the trace of the Cauchy-Green deformation tensor such that:

$$I_1 = tr(F^T F) = \lambda_1^2 + \lambda_2^2 + \lambda_3^2 \quad (14)$$

where F defines the deformation tensor and $\lambda_1$, $\lambda_2$, $\lambda_3$ define the principal stretches in axial, radial and circumferential, respectively (see J. Gwinner, *Acta Applicandae Mathematica*, vol. 11, pp. 191-193, February 1988). Following the assumption of vanishing radial and circumferential stress, then the axial principal stress of interest can be formulated as a partial derivative with respect to the axial principal stretch with Equations (13) and (14) as:

$$\sigma_1 = \frac{\partial W}{\partial \lambda_1} - \frac{p}{\lambda_1} = 2C_1(\lambda_1 - \lambda_1^{-3}) \quad (15)$$

where p is a Lagrange multiplier (see P. Polygerinos et al., *IEEE Transactions on Robotics*, vol. 31, pp. 778-789, June 2015).

Bending

Figure 13:
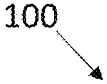
FIG. 13 shows example experimental model parameters of an elastomer robot in accordance with some embodiments.
Figure 13:
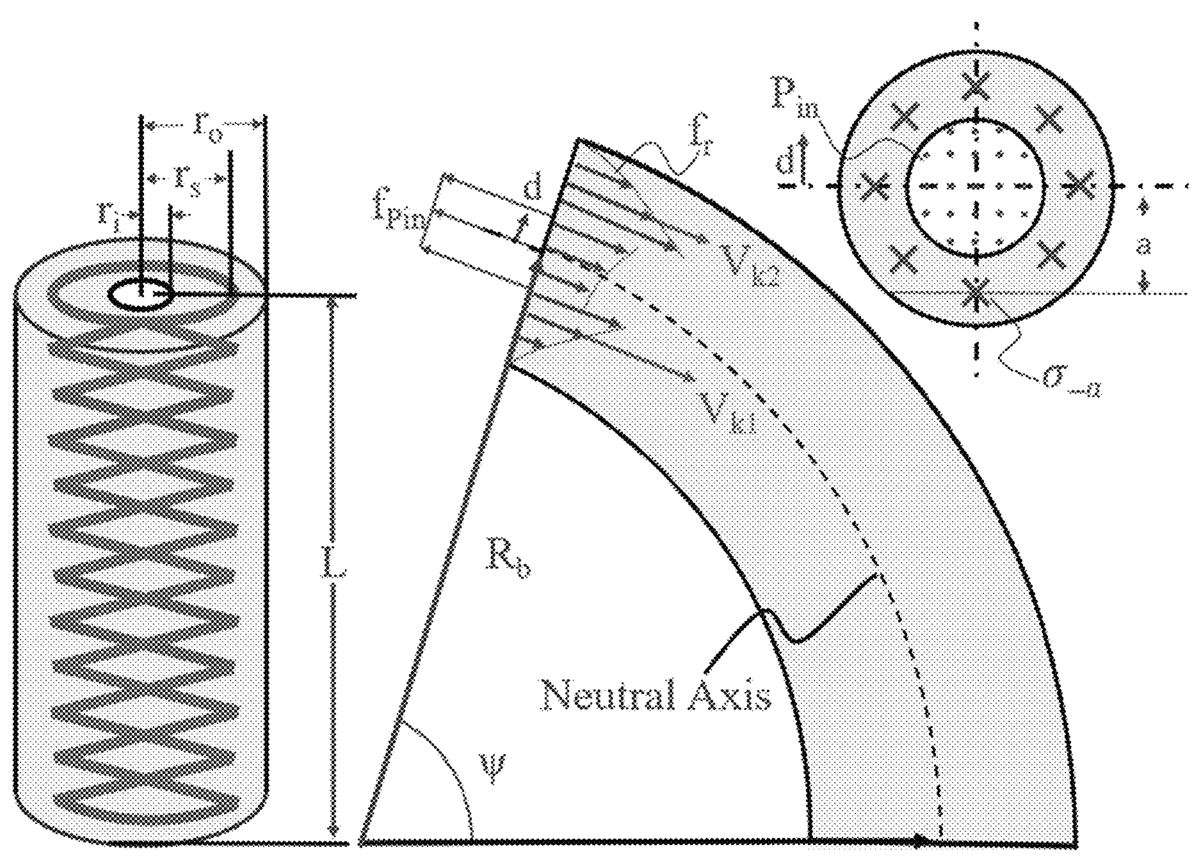

FIG. 13 shows example experimental model parameters of an elastomer robot in accordance with some embodiments. Constant curvature modeling simplifies that shape to be defined by two parameters, the bending radius R and the bending angle θ.

Assuming moment and force equilibrium, the equations that need to be solved are:

$$\sum M_{internal} - \sum M_{applied} = 0 \quad (16)$$

$$\sum F_{internal} - \sum F_{applied} = 0$$

Furthermore, note that because $\Sigma M_{internal}$ is zero by symmetry of pressure forces around the center plane of the robot 100, the moment equilibrium condition simplifies to:

$$\sum M_{internal} = 0 \quad (17)$$

Let θ and R define the bending angle and the bending radius, respectively, as shown in FIG. 13. By the geometry of bending the axial principal stretch can be defined as:

$$\lambda_1 = \frac{\psi(R_b + d)}{L} \quad (18)$$

Also note that because neither side of the bending robot 100 is constrained, the principal stretch definition cannot be further simplified by a constant geometric relationship between R and θ. In planar bending, the principal stretch is constant along the same distance d away from the neutral plane as observed in FIG. 13. Then with the known axial neo-Hookean stress definition of Equation (15), stress $\sigma_d$ given bending shape $R_b$ and $\psi$ at d distance away from the neutral plane is defined by:

$$\sigma_d = 2C_1\left[\frac{\psi(R_b+d)}{L} - \left(\frac{L}{\psi(R_b+d)}\right)^3\right] \tag{19}$$

Then resulting from geometry and integrating stress over the circular cross section, the internal force and moment on the center plane from silicone cylinder of radius r is as follows:

$$F_r(R_b, \psi) = \int_{-r}^{r} \sigma_d \cdot 2\sqrt{r_i^2 - d^2} \cdot \delta d \tag{20}$$

$$M_r(R_b, \psi) = \int_{-r}^{r} \sigma_d \cdot 2\sqrt{r_i^2 - d^2} \cdot d \cdot \delta d$$

Additionally, the internal structure applies force and moment on the distal end. With the assumptions previously outlined, the force and moment applied on the distal cap is linear with the axial principal stretch. To account for asymmetry, let $\bar{k}$ define the axial stiffness of a uniform thickness half of an internal structure 105 with top view radius of $R_{IS}$ found from Equation (12). Then the force and moment applied by the half internal structure on the distal cap can be defined as the following:

$$F_r(R_b, \psi) = [\lambda - 1]k \tag{21}$$

$$M_r(R_b, \psi) = [\lambda - 1]k \cdot R_{IS}$$

The internal force and moments applied by the silicone and internal structure fully define $\Sigma M_{internal}$ and $\Sigma F_{internal}$. By observing the robot structure outlined in FIG. 13 and the assumptions of tubular displacement of silicone by the internal structure 105, $$\sum F_{internal}(R_b, \psi) = F_{r_0}(R_b, \psi) - F_{r_s+t_{is}}(R_b, \psi) + F_{r_s-t_{is}}(R_b, \psi) - F_{r_i}(R_b, \psi) + F_{k1}(R_b, \psi) + F_{k2}(R_b, \psi) \tag{22}$$

$$\sum M_{internal}(R_b, \psi) = M_{r_0}(R_b, \psi) - M_{r_s+t_{is}}(R_b, \psi) + M_{r_s-t_{is}}(R_b, \psi) - M_{r_i}(R_b, \psi) + M_{k1}(R_b, \psi) - M_{k2}(R_b, \psi)$$

To solve for the equilibrium conditions of Equation (16), the applied force should also be assessed. Assuming the only significant applied force component comes from the pressure acting on the distal cap, the applied force component can be found as:

$$\sum F_{applied} = (P_{in} - P_{atm})A_{distal} \tag{23}$$

where by geometry, the distal cap area is defined by:

$$A_{distal} = \frac{\pi r_i^2}{4} \tag{24}$$

Applying the results of Equations (17), (22) and (23) to the original equilibrium conditions of Equation (16), the bending radius and the bending angle can be solved numerically based on design parameters.

EXPERIMENTAL SETUPS AND PROCEDURES

To evaluate the performance of the developed modeling approach as well as the fabricated internal structure 105 and robot 100, two experimental setups were utilized. The following sections briefly describe these setups and the experimental protocol.

Figure 14:
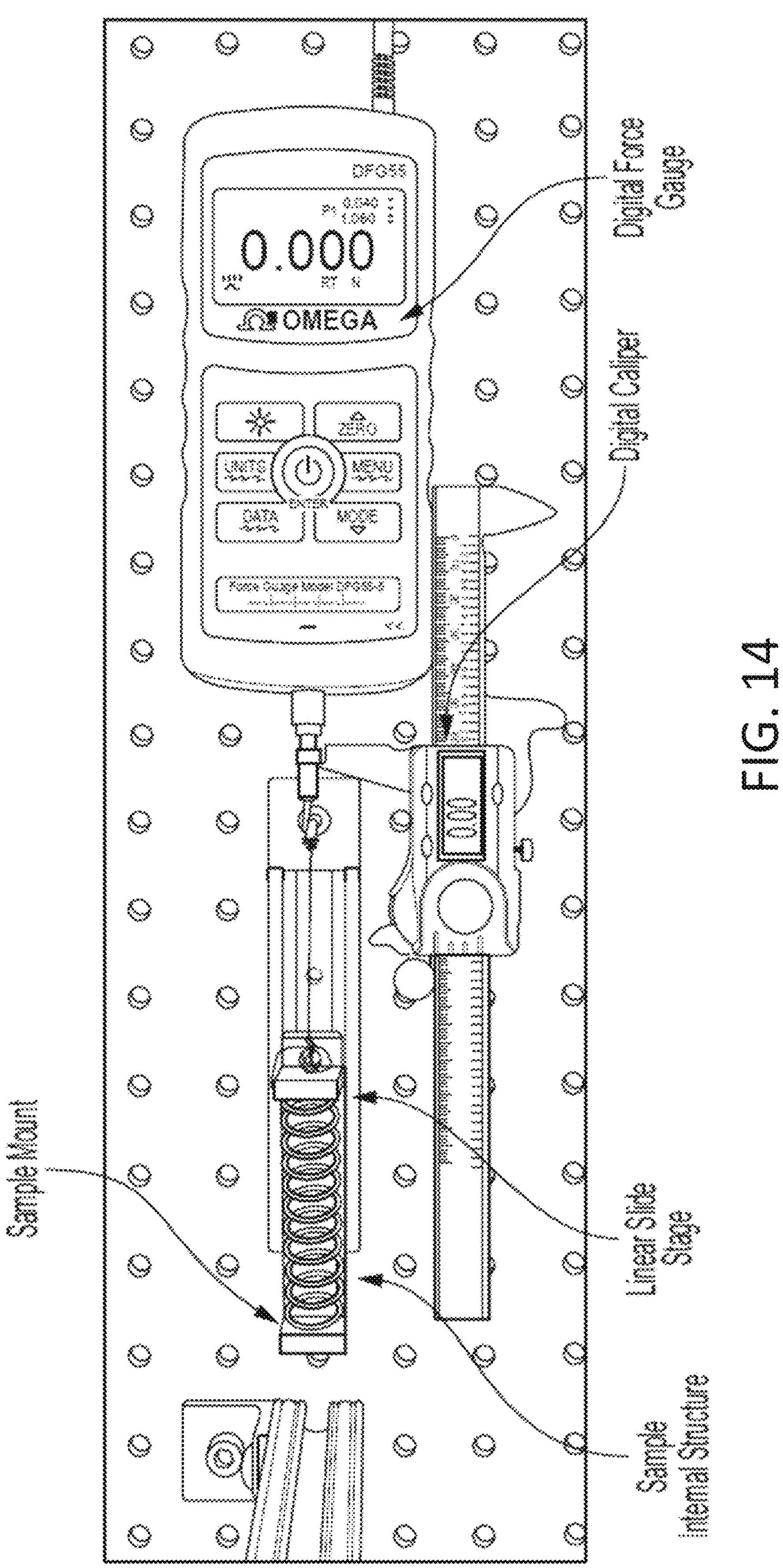
FIG. 14 shows an example experimental setup for measuring axial stiffness of an elastomer robot in accordance with some embodiments.

Stiffness Testbed:

FIG. 14 shows an example experimental setup for measuring axial stiffness of an elastomer robot 100 in accordance with some embodiments. As shown in FIG. 14, a single degree of freedom testbed was prepared to find the axial stiffness of the internal structure and compare the obtained experimental result with the calculated stiffness using the Castigliano's method. To perform the experiments, a digital caliper was connected to a force gauge (DFG55, Omega Engineering) in order to measure displacement and force in the axial direction, respectively. The printed internal structure 105 was fixed on one end and connected to a linear carriage stage on the other. The structure was then pulled at 5 mm increments up to 40 mm or to failure. The average gradient in the linear region of the force-elongation plots of five trials was taken as measured stiffness. To demonstrate practical efficacy of the method, three different stiffness values were set, then the model was used to design the internal structure to match the stiffness. It was determined with the model that to achieve stiffness of 5 N/m, 25 N/m and 125 N/m, the SLA Flexible Resin internal structures 105 should have the diameters of 0.74 mm, 1.11 mm and 1.66 mm respectively. The angle of the analyzed segment with respect to the ground axis ($\alpha$) was taken as 15° (0.262 rad). Integration in Equations (1) was taken from 0 rad to $\pi/2$ rad. The radius of the internal structure was considered as 5.0 mm as designed. The samples were prepared with 10 joints along one side (n=10).

Figure 15:
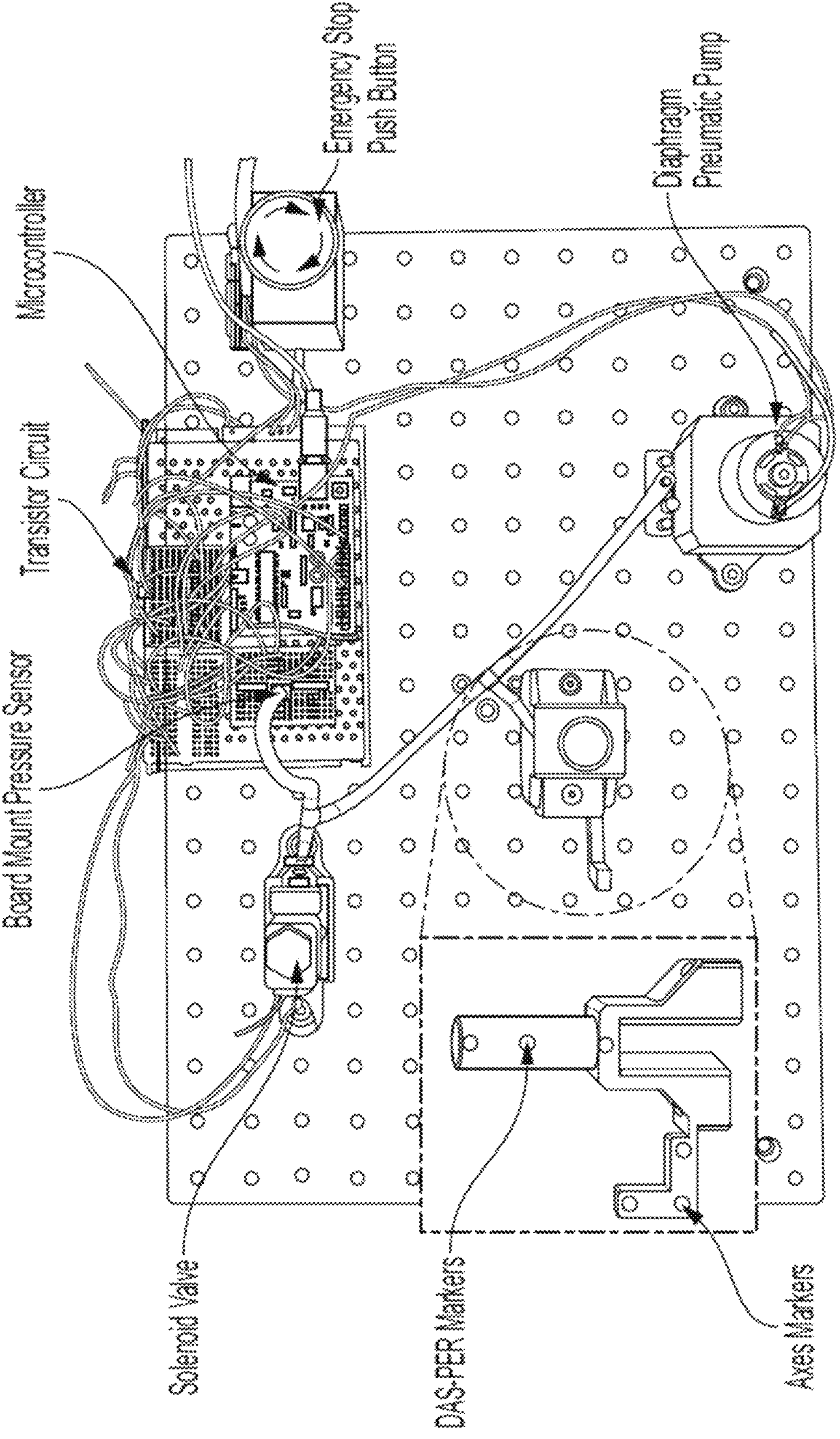
FIG. 15 shows an example experimental setup for validating an actuation behavior model of an elastomer robot in accordance with some embodiments.

Actuation Testbed:

FIG. 15 shows an example experimental setup for validating an actuation behavior model of an elastomer robot in accordance with some embodiments. Two robots 100 were fabricated to validate the model. As shown in FIG. 15, sample robots 100 were secured on a controlled testbed. A pneumatic diaphragm pump (D028B, Airpo™), a solenoid valve (USS2-00005, U.S. Solid), a pressure sensor (SSCDANT150PGAA5, Honeywell International Inc.), and the robot 100 were connected. A microcontroller (Arduino UNO, Arduino AG) was used to control the pump and the valve. Three red markers were placed along the robot 100 sample to detect the actuated shape. Three additional red markers were placed on the base 3 cm from each other to define the axes and scale. Pressure was increased incrementally by 10 kPa until failure. There was a 5 second delay at each pressure to let the robot 100 settle into its equilibrium state. Two robots 100 were tested to assess the model's ability to predict actuation behavior of the robots 100. The design parameters were selected to display different extension and bending behaviors. The first robot (DAS-PER A) was embedded with an internal structure that has 1.5 mm and 2.0 mm helices, and the second robot (DAS-PER B) had an internal structure with 1.0 mm and 2.0 mm helices. In reference to FIG. 2, $R_{is}$, $t_{is}$, and $\alpha$ were designed to be 7.5 mm, 2 mm and 15° respectively. In reference to FIG. 13, L, $r_i$ and $r_o$ were designed to be 50 mm, 4.5 mm and 10 mm respectively for both samples.

EXPERIMENTAL RESULTS

Figure 16:
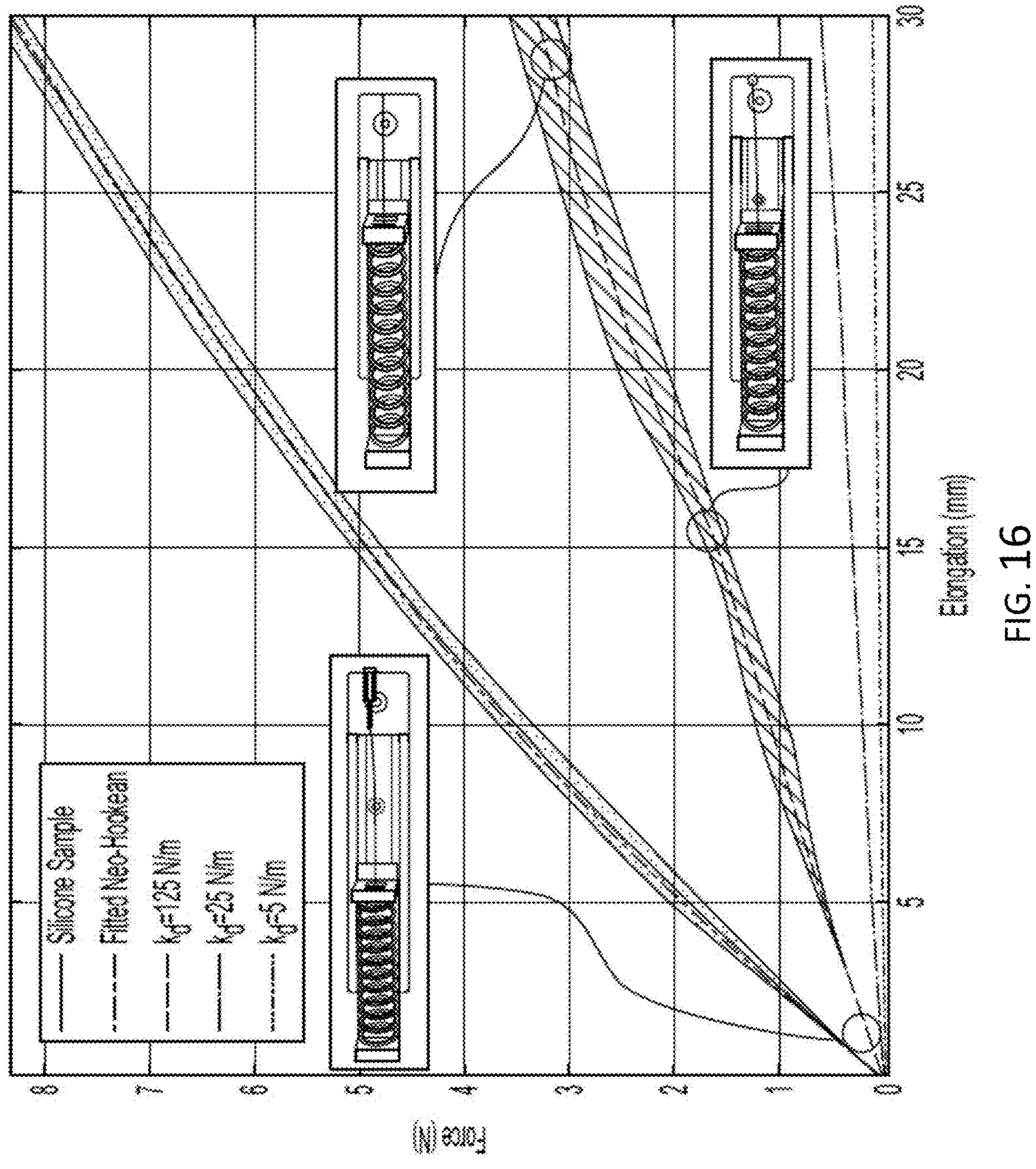
FIG. 16 is a plot showing example experimental results in accordance with some embodiments.

FIG. 16 is a plot showing example experimental results in accordance with some embodiments and FIG. 17 is a table showing example experimental results compared to the model of an elastomer robot in accordance with some embodiments. The stiffness measurement results validate the linear internal energy model of the internal structure 105, with $k_d$ being the desired stiffness based on the model. FIG. 16 shows the obtained experimental elongations versus exerted forces using the stiffness testbed for the three example internal structures 105. The shaded region around each plot denotes the deviation of the 5 trials from the calculated average. Also, the table of FIG. 17 summarizes the comparison of the calculated stiffness based on the model and obtained experimental results. The input parameters into the derived model were held constant among the tested internal structure except for the cross-sectional diameter. The material properties and their corresponding parameter values are stated in the table of FIG. 11. Additionally, the same experiment was conducted with a silicone sample with cross-sectional area and length of 250 $mm^2$ and 42 mm. $C_1$ was fitted to be 10.6 kPa with $R^2$ value of 0.998 as shown in FIG. 16.

The first sample robot 100 was made from Flexible Resin (FR) (PLA), had a desired stiffness ($k_d$) of 5 N/m, a manufactured coil diameter ($D_m$) of 0.74 mm, and experimental stiffness ($k_e$) of 4.35 N/m, and an error of 13.00%. The second sample robot 100 was made from Flexible Resin (FR) (PLA), had a desired stiffness ($k_d$) of 25 N/m, a manufactured coil diameter ($D_m$) of 1.11 mm, and experimental stiffness ($k_e$) of 22.2 N/m, and an error of 11.28%. The third sample robot 100 was made from Flexible Resin (FR) (PLA), had a desired stiffness ($k_d$) of 125 N/m, a manufactured coil diameter ($D_m$) of 1.66 mm, and experimental stiffness ($k_e$) of 112.2 N/mm, and an error of 10.24%.

Figure 18:
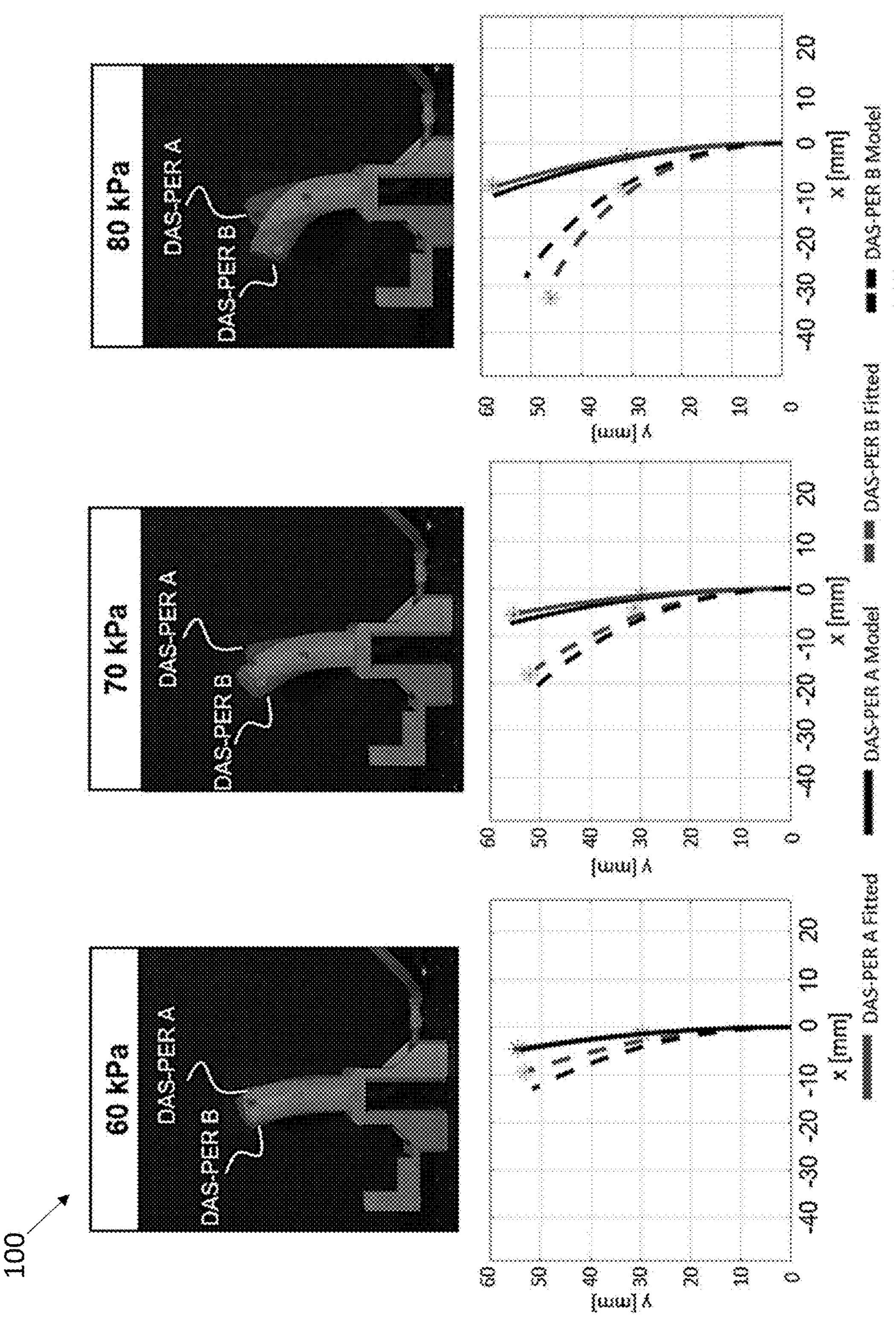
FIG. 18 shows example experimental results in accordance with some embodiments.

The actuation profiles of the robots 100 obtained from the experiments performed with the testbed shown in FIG. 15 are plotted in FIG. 18. Three points on the robot samples were plotted at 60 kPa, 70 kPa and 80 kPa internal pressure and a constant curvature line was fitted. These plots were overlaid with model predictions. The figure also includes images that were processed to obtain the results.

Observation of FIG. 16 indicates that the force-elongation profiles of the three internal structures 105 closely follow the model's assessment of structure stiffness in relation to cross-sectional diameter. The stiffness of the internal structure 105 increases with an increase in cross-sectional diameter in a predictable manner. It can also be observed that large changes in the stiffness values can be achieved with relatively small change in diameters. This is partially because the moment of inertia calculations amplifies changes in diameter. The fabrication procedure was also simplified. From the table of FIG. 17, it is also evident that the experimentally obtained stiffness of the internal structures closely matches the calculated stiffness utilizing the Castigliano's energy method. The error was found to be roughly around 10% independent of the stiffness scale.

The partially rigid internal structure 105 meant that robot 100 could be molded in a single step, reducing the fabrication time by at least the curing time of the silicone. The fabrication procedure also did not depend on the skill or intuition of the fabricator with approximately 30 minutes of active labor involving two mold components. Because the baseline fabrication time for PEAs with embedded fiber helices can vary significantly among fabricators based on experience and skill, it is difficult to precisely quantify reduction in fabrication time. However, based on the rough benchmark reported in literature, robot 100 fabrication represents an 80% reduction in mold parts compared to single chamber PEAs and an 50% reduction in active labor time.

FIG. 18 effectively validates the efficacy of the robot 100 method. The mean percentage error for the model to the observed robot 100 shape (determined by the fitted curvature) was <12% for the DAS-PER A sample and <18% for the DAS-PER B sample. The strong results underscore not only the efficacy of the modeling but also the reliability of the presented design and fabrication method. Furthermore, two observations can be made. First, despite the relatively small 0.5 mm change in diameter of the internal structure greatly affected the bending and extension behavior of the robot 100. Secondly, the results also show that the primary mode of deformation changes based on the stiffness difference on each side of the internal structure 105. When the difference is large such as with DAS-PER B configuration, actuation behavior is dominated by bending. When the difference is smaller such as with the DAS-PER A configuration, the actuation behavior is dominated by extension. In both cases, robot 100 actuation behavior displayed little to no observable ballooning effect or changes in the overall diameter.

The accuracy of the model and the displayed sensitivity to internal structure design parameters ultimately validate the method's ability to enable fabricators to tune the behavior of PEAs to achieve diverse set of concurrent bending and extension profiles. The design and model-based framework disclosed can effectively enable PEAs to be tuned optimized to for the environment.

The following references are incorporated herein by reference in their entirety:

L. Cao, X. Li, P. T. Phan, A. M. H. Tiong, J. Liu, and S. J. Phee, "A Novel Robotic Suturing System for Flexible Endoscopic Surgery," in 2019 *International Conference on Robotics and Automation* (*ICRA*), pp. 1514-1520 May 2019.

M. Kamata, S. Yamazaki, Y. Tanise, Y. Yamada, and T. Nakamura, "Morphological change in peristaltic crawling motion of a narrow pipe inspection robot inspired by earthworm's locomotion," *Advanced Robotics*, vol. 32, pp. 386-397, April 2018. Publisher: Taylor & Francis.

Y. Elsayed, A. Vincensi, C. Lekakou, T. Geng, C. M. Saaj, T. Ranzani, M. Cianchetti, and A. Menciassi, "Finite Element Analysis and Design Optimization of a Pneumatically Actuating Silicone Module for Robotic Surgery Applications," *Soft Robotics*, vol. 1, pp. 255-262, October 2014. Publisher: Mary Ann Liebert, Inc., publishers.

C. Lee, M. Kim, Y. J. Kim, N. Hong, S. Ryu, H. J. Kim, and S. Kim, "Soft robot review," *International Journal of Control, Automation and Systems*, vol. 15, pp. 3-15, February 2017.

A. D. Marchese and D. Rus, "Design, kinematics, and control of a soft spatial fluidic elastomer manipulator," *The International Journal of Robotics Research*, vol. 35, pp. 840-869, October 2015. Publisher: SAGE Publications Ltd STM.

P. Polygerinos, Z. Wang, J. T. B. Overvelde, K. C. Galloway, R. J. Wood, K. Bertoldi, and C. J. Walsh, "Modeling of Soft Fiber Reinforced Bending Actuators," *IEEE Transactions on Robotics*, vol. 31, pp. 778-789, June 2015.

S. Hashemi, D. Bentivegna, and W. Durfee, "Bone-Inspired Bending Soft Robot," *Soft Robotics*, July 2020. Publisher: Mary Ann Liebert, Inc., publishers.

R. Deimel and O. Brock, "A novel type of compliant and underactuated robotic hand for dexterous grasping," *The International Journal of Robotics Research*, vol. 35, pp. 161-185, August 2015. Number: 1-3 Publisher: SAGE Publications Ltd STM.

K. Suzumori, T. Maeda, H. Wantabe, and T. Hisada, "Fiberless flexible microactuator designed by finite-element method," *IEEE/ASME Transactions on Mechatronics*, vol. 2, pp. 281-286, December 1997.

P. Polygerinos, S. Lyne, Z. Wang, L. F. Nicolini, B. Mosadegh, G. M. Whitesides, and C. J. Walsh, "Towards a soft pneumatic glove for hand rehabilitation," in 2013 *IEEE/RSJ International Conference on Intelligent Robots and Systems*, pp. 1512-1517 November 2013. Journal Abbreviation: 2013 IEEE/RSJ International Conference on Intelligent Robots and Systems.

B. Mosadegh, P. Polygerinos, C. Keplinger, S. Wennstedt, R. F. Shepherd, U. Gupta, J. Shim, K. Bertoldi, C. J. Walsh, and G. M. Whitesides, "Pneumatic Networks for Soft Robotics that Actuate Rapidly," *Advanced Functional Materials*, vol. 24, no. 15, pp. 2163-2170, 2014. https://onlinelibrary.wiley.com/doi/pdf/10.1002/adfm.201303288.

R. F. Shepherd, F. Ilievski, W. Choi, S. A. Morin, A. A. Stokes, A. D. Mazzeo, X. Chen, M. Wang, and G. M. Whitesides, "Multigait soft robot," *Proceedings of the National Academy of Sciences,* 2011. Publisher: National Academy of Sciences eprint: https://www.pnas.org/content/early/2011/11/21/1116564108.full.pdf.

F. Connolly, C. J. Walsh, and K. Bertoldi, "Automatic design of fiber-reinforced soft actuators for trajectory matching," *Proceedings of the National Academy of Sciences*, vol. 114, no. 1, pp. 51-56, 2017. Publisher: National Academy of Sciences eprint: https://www.pnas.org/content/114/1/51.full.pdf.

F. Connolly, P. Polygerinos, C. J. Walsh, and K. Bertoldi, "Mechanical Programming of Soft Actuators by Varying Fiber Angle," *Soft Robotics*, vol. 2, pp. 26-32, March 2015. Publisher: Mary Ann Liebert, Inc., publishers.

J. Fras, J. Glowka, and K. Althoefer, "Instant soft robot: A simple recipe for quick and easy manufacturing," in 2020 *3rd IEEE International Conference on Soft Robotics (RoboSoft)*, pp. 482-488, July 2020. Journal Abbreviation: 2020 3rd IEEE International Conference on Soft Robotics (RoboSoft).

Z. Wang, P. Polygerinos, J. T. B. Overvelde, K. C. Galloway, K. Bertoldi, and C. J. Walsh, "Interaction Forces of Soft Fiber Reinforced Bending Actuators," *IEEE/ASME Transactions on Mechatronics*, vol. 22, pp. 717-727, April 2017.

Y. Sun, Y. S. Song, and J. Paik, "Characterization of silicone rubber based soft pneumatic actuators," in 2013 *IEEE/RSJ International Conference on Intelligent Robots and Systems*, pp. 4446-4453 November 2013. ISSN: 2153-0866.

D. R. Ellis, M. P. Venter, and G. Venter, "Soft Pneumatic Actuator with Bimodal Bending Response Using a Single Pressure Source," *Soft Robotics*, August 2020. Publisher: Mary Ann Liebert, Inc., publishers.

T. Nakajima, T. Yamaguchi, S. Wakabayashi, T. Arie, S. Akita, and K. Takei, "Transformable Pneumatic Balloon-Type Soft Robot Using Attachable Shells," *Advanced Materials Technologies*, vol. 5, p. 2000201, July 2020. Publisher: John Wiley & Sons, Ltd.

P. Preechayasomboon and E. Rombokas, "Negshell casting: 3D-printed structured and sacrificial cores for soft robot fabrication," *PLOS ONE*, vol. 15, p. e0234354, June 2020. Publisher: Public Library of Science.

P. Huy Nguyen, S. Sridar, W. Zhang, and P. Polygerinos, "Design and control of a 3-chambered fiber reinforced soft actuator with off-the shelf stretch sensors," *International Journal of Intelligent Robotics and Applications*, April 2017.

P. Polygerinos, N. Correll, S. A. Morin, B. Mosadegh, C. D. Onal, K. Petersen, M. Cianchetti, M. T. Tolley, and R. F. Shepherd, "Soft Robotics: Review of Fluid-Driven Intrinsically Soft Devices; Manufacturing, Sensing, Control, and Applications in Human-Robot Interaction," *Advanced Engineering Materials*, vol. 19, December 2017.

F. Beer, E. Jr. Johnston, J. DeWolf, and D. Mazurek, *Mechanics of Materials*. McGraw-Hill Education, 2011.

J. Gwinner, "Non-linear elastic deformations," *Acta Applicandae Mathematica*, vol. 11, pp. 191-193, February 1988.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention.

What is claimed is:

1. A programmable elastomer robot, comprising:

a flexible internal structure comprising a first flexible material, wherein the internal structure is tunable, and wherein the flexible internal structure comprises a coil having an asymmetric axial stiffness; and a flexible external structure comprising a second flexible material, attached to the internal structure, including an aperture configured to accept a fluid, wherein the external structure is tunable.

2. The robot of claim 1, wherein the internal structure includes at least one section, wherein the at least one section includes at least one diameter, wherein the at least one diameter is a varying value.

3. The robot of claim 1, wherein the internal structure is cylindrical.

4. The robot of claim 1, wherein the internal structure is a quad-helical coil, wherein the quad-helical coil includes a first coil section with a first coil diameter, and a second coil section with a second coil diameter.

5. The robot of claim 1, wherein the internal structure is conical.

6. The robot of claim 1, wherein the internal structure is a conical coil including a first coil section with a first coil diameter, a second coil section with a second coil diameter, a third coil section with a third coil diameter, and a fourth coil section with a fourth coil diameter.

7. The robot of claim 1, wherein the internal structure is sinusoidal.

8. The robot of claim 1, wherein the internal structure is a sinusoidal coil including a first coil section with a first coil diameter, and a second coil section with a second coil diameter.

9. The robot of claim 1, wherein the robot extends, bends, or extends and bends concurrently.

10. The robot of claim 1, wherein the robot has a preprogrammed actuation behavior based on tunable parameters provided by a model.

11. The robot of claim 10, wherein the tunable parameters provided by the model are variable parameters.

12. The robot of claim 1, wherein the internal structure is self-supporting.

13. The robot of claim 1, wherein the internal structure comprises flexible resin.

14. The robot of claim 1, wherein the external structure comprises silicone rubber.

15. The robot of claim 1, wherein the external structure has a varying thickness.

16. The robot of claim 1, further comprising an internal cavity.

17. A method of using a programmable elastomer robot, comprising:

providing the programmable elastomer robot of claim 1; and supplying a fluid via the aperture, configured to apply to a force to actuate the robot.

* * * * *